US008541187B2

(12) United States Patent
Passavant et al.

(10) Patent No.: US 8,541,187 B2
(45) Date of Patent: Sep. 24, 2013

(54) SYSTEMS AND METHODS FOR DETECTING ANIMAL PREGNANCY

(75) Inventors: Charles W. Passavant, Moscow, ID (US); Joshua R. Branen, Moscow, ID (US); Robert Garth Sasser, Mosco, ID (US); Jeremy Michael Howard, Moscow, ID (US)

(73) Assignee: Bio Tracking, LLC, Moscow, ID (US)

( * ) Notice: Subject to any disclaimer, the term of this patent is extended or adjusted under 35 U.S.C. 154(b) by 0 days.

(21) Appl. No.: 13/038,248

(22) Filed: Mar. 1, 2011

(65) Prior Publication Data

US 2012/0225438 A1    Sep. 6, 2012

(51) Int. Cl.
*G01N 33/53* (2006.01)
(52) U.S. Cl.
CPC .................................. *G01N 33/53* (2013.01)
USPC ............ 435/7.9; 435/7.1; 435/7.92; 436/510; 436/518

(58) Field of Classification Search
None
See application file for complete search history.

(56) References Cited

U.S. PATENT DOCUMENTS

| | | | |
|---|---|---|---|
| 4,402,872 A | 9/1983 | Bohn | |
| 4,554,256 A | 11/1985 | Sasser et al. | |
| 4,668,621 A | 5/1987 | Doellgast | |
| 4,705,748 A | 11/1987 | Sasser et al. | |
| 5,420,016 A * | 5/1995 | Boguslaski et al. | 435/12 |
| 5,559,097 A | 9/1996 | Sasser | |
| 6,860,859 B2 | 3/2005 | Mehrotra et al. | |
| 6,869,770 B1 | 3/2005 | Roberts et al. | |
| 6,949,629 B2 | 9/2005 | Newman et al. | |
| 7,125,728 B2 * | 10/2006 | Ott | 436/510 |
| 7,393,696 B2 | 7/2008 | Roth et al. | |
| 7,501,256 B2 | 3/2009 | Colgin et al. | |
| 7,575,861 B2 | 8/2009 | Lucy et al. | |
| 7,604,950 B2 | 10/2009 | Mathialagan et al. | |
| 7,659,087 B2 | 2/2010 | Colgin et al. | |
| 7,670,789 B2 | 3/2010 | Colgin et al. | |
| 7,687,281 B2 * | 3/2010 | Roth et al. | 436/510 |
| 7,763,432 B2 | 7/2010 | Roberts et al. | |
| 7,842,513 B2 | 11/2010 | Colgin et al. | |
| 2003/0059951 A1 | 3/2003 | Frushour et al. | |
| 2004/0266697 A1 | 12/2004 | McSweeney et al. | |
| 2005/0100975 A1 | 5/2005 | Roberts et al. | |
| 2006/0199235 A1 | 9/2006 | Lucy et al. | |
| 2007/0009969 A1 | 1/2007 | Ott | |
| 2007/0166773 A1 | 7/2007 | Roberts et al. | |
| 2007/0184558 A1 | 8/2007 | Roth et al. | |
| 2007/0249003 A1 | 10/2007 | Colgin et al. | |
| 2008/0003695 A1 | 1/2008 | Mathialagan et al. | |
| 2008/0026384 A1 | 1/2008 | Hansen | |
| 2008/0312151 A1 | 12/2008 | Colgin et al. | |
| 2009/0155813 A1 | 6/2009 | Colgin et al. | |
| 2009/0258375 A1 | 10/2009 | Green et al. | |
| 2010/0120677 A1 | 5/2010 | Colgin et al. | |
| 2010/0136588 A1 | 6/2010 | Colgin et al. | |
| 2010/0184070 A1 | 7/2010 | Colgin et al. | |
| 2011/0076705 A1 | 3/2011 | Mathialagan et al. | |

FOREIGN PATENT DOCUMENTS

| | | |
|---|---|---|
| EP | 0406281 B1 | 7/1992 |
| FR | 2628743 A1 | 9/1989 |
| NZ | 228344 A | 2/1992 |
| WO | WO8908668 A1 | 9/1989 |
| WO | WO03093493 A2 | 11/2003 |
| WO | WO2009076632 A1 | 6/2009 |

OTHER PUBLICATIONS

Piechotta et al., Comparison of Commercial ELISA Blood Tests for Early Pregnancy Detection in Dairy Cows, Journal of Reproduction and Development, vol. 57, No. 1, Feb. 2011, pp. 72-75. ( Published online in J-STAGE: Sep. 24, 2010).*
Voller, The Enzyme Linked Immunosorbent Assay (ELISA), Diagnostic Horizons, vol. 2, No. 1, Feb. 1978.*
Erickson et al., Immunoassay for Quantifying Squamous Cell Carcinoma antigen in Serum, Brief Communications, Clinical Chemistry 56:9 pp. 1496-1499, 2010.*
James Edmund Butler, "Isolation and Partial Characterization of Two Bovine Pregnancy-Associated Proteins" thesis, 1980, University of Idaho, Moscow, Idaho USA.
Butler et al., "Detection and Partial Characterization of Two Bovine Pregnancy-Specific Proteins", article in Biology of Reproduction, 1982, vol. 26, pp. 925-933.
Camous et al., "Purification of One Bovine Pregnancy-Specific Protein by High-Performance Liquid Chromatography (HPLC)", abstract, Proceedings Bard Workshop, Maternal Recognition of Pregnancy and Maintenance of the Corpus Luteum, 1988, Jerusalem.
Eckblad et al., "Localization of pregnancy-specific protein B (PSPB) in bovine placental cells using glucose oxidase-anti-glucose oxidase immunohistochemical stain", article in J. Anim. Sci. Suppl., 1985, vol. 61, pp. 149-150.
Gonzaléz et al., "Pregnancy-Associated Glycoproteins (PAG) Detection in Milk Samples for Pregnancy Diagnosis in Dairy Goats", article in Theriogenology, 2001, vol. 56, pp. 671-676.
Green et al., "Measurement of interferon-tau (IFN-tau) stimulated gene expression in blood leukocytes for pregnancy diagnosis within 18-20 d after insemination in dairy cattle", article in Animal Reproduction Science, 2010, vol. 121, pp. 24-33.
William C. Hamilton, "Pregnancy-Associated Antigens of Early Pregnancy in Cattle", thesis, Apr. 1979, University of Idaho, Moscow, Idaho USA.

(Continued)

*Primary Examiner* — Gary W Counts
(74) *Attorney, Agent, or Firm* — Kolisch Hartwell, P.C.

(57) ABSTRACT

Testing systems and methods are disclosed for detecting a pregnancy marker of an animal. A test kit may include a first standard with a first concentration of the marker, a second standard with a second concentration of the marker lower than the first concentration, and at least three test surfaces coated with a biomolecular recognition element selected to bind with the marker. The test may also include a reagent solution with a conjugated biomolecular recognition element that binds with the marker, and a visual indicator that produces a visually detectable change when reacting with the conjugated biomolecular recognition element bound to each test surface. A detectable change generated by the marker from the sample with an intensity greater than the first concentration yields a pregnant result, lower than the second concentration yields a not pregnant result, and between the first and second concentrations yields a retest result.

29 Claims, 3 Drawing Sheets

(56) References Cited

OTHER PUBLICATIONS

Hicks et al., "Expression of the uterine Mx protein in cyclic and pregnant cows, gilts, and mares", article in Journal of Animal Science, 2003, vol. 81, pp. 1552-1561.

Howard et al., "BioPRYN a Blood-Based Pregnancy Test for Managing Breeding and Pregnancy in Cattle", Proceedings, Western Section, American Society of Animal Science, 2007, vol. 58, pp. 295-298.

Hughes et al., "Aspartic Proteinase Phylogeny and the Origin of Pregnancy-Associated Glycoproteins", article in Society for Molecular Biology and Evolution, 2003, vol. 20, No. 11, pp. 1940-1945.

Humblot et al., "Diagnosis of Pregnancy by Radioimmunoassy of a Pregnancy-Specific Protein in the Plasma of Dairy Cows", article in Thereiogenology, Aug. 1988, vol. 30, No. 2, pp. 257-267.

Kristen Ann Ivani, "Diagnosis of Pregnancy by Radioimmunoassay of a Pregnancy-Specific Protein in Serum of Cows", thesis, Jun. 1984, University of Idaho, Moscow, Idaho USA.

Catherine Patricia King, "Quantification, Isolation and Characterization of Pregnancy-Specific Protein B (PSPB) in Bovine Colostrum and Postpartum Milk", thesis, Apr. 1996,University of Idaho, Moscow, Idaho USA.

Lynch et al., "The Cloning and Expression of the Bovine Pregnancy Protein B (bPSPB) Gene", article in Biol Reprod Suppl., vol. 46 (Suppl. 1), p. 73, 1992.

Noyes et al., "Accuracy of Pregnancy Detection by Serum Protein (PSPB) in Elk", Wildlife Society Bulletin, 1997, vol. 25, No. 3, pp. 695-698.

Prakash et al., "Characterization of the bovine pregnancy-associated glycoprotein gene family—analysis of gene sequences, regulatory regions within the promoter and expression of selected genes", article in BMC Genomics, Apr. 24, 2009, vol. 10, 17 pages.

Sasser et al., "Characteristics of pregnancy-specific protein B in cattle", article in Journals of Reproduction & Fertility Ltd Suppl., 1989, vol. 37 pp. 109-113.

Sasser et al., "Detection of early pregnancy in domestic ruminants", article in Journals of Reproductivity & Fertility Ltd Suppl., 1987, vol. 34, pp. 261-271.

Sasser et al., "Detection of Pregnancy by Radioimmunoassay of a Novel Pregnancy-Specific Protein in Serum of Cows and a Profile of Serum Concentrations during Gestation", article in Biology of Reproduction, 1986, vol. 35, pp. 936-942.

Semambo et al., "Pregnancy-Specific Protein B and Progesterone in Monitoring Viability of the Embryo in Early Pregnancy in the Cow After Experimental Infection with Actinomyces Pyogenes", article in Theriogenology, 1992, vol. 37, pp. 741-748.

Stabenfeldt et al., "An Oestrogen Conjugate Enzyme Immunoassay for Monitoring Pregnancy in the Mare: Limitations of the Assay Between Days 40 and 70 of Gestation", article in Journals of Reproduction & Fertility Ltd Suppl., 1991, vol. 44, pp. 38-44.

Szafranska et al., "Biodiversity of multiple Pregnancy-Associated Glycoprotein (PAG) family: gene cloning and chorionic protein purification in domestic and wild eutherians (Placentalia)—a review", article in Reprod. Nutr. Dev., 2006, vol. 5, pp. 481-502.

Willard et al., "Detection of fetal twins in sheep using a radioimmunoassay for pregnancy-specific protein B", article in Journal of Animal Science, 1995, vol. 73, pp. 960-966.

Xie et al., "Identification of the Major Pregnancy-Specific Antigens of Cattle and Sheep as Inactive Members of the Aspartic Proteinase Family", article in Proceedings of the National Academy of Sciences of the United States of America, Nov. 15, 1991, vol. 88, No. 22, pp. 10247-10251.

Zoli et al., "Purification and Characterization of a Bovine Pregnancy-Associated Glycoprotein", article in Biology of Reproduction, 1991, vol. 45, pp. 1-10.

Green et al., "Technical note: A rapid enzyme-linked immunosorbent assay blood test for pregnancy in dairy and beef cattle", article in American Dairy Science Association, 2009, pp. 3819-3824.

Garth Sasser, Grant Proposal to Idaho Research Foundation, Apr. 27, 1984, 3 pages.

Kiracofe et al., "Pregnancy-specific protein B in serum of postpartum beef cows", article in Journal of Animal Science, 1993, vol. 71, pp. 2199-2205.

Sasser et al., "BioPRYN, a Measure of Pregnancy-Specific Protein B for Detection of Pregnancy in Ruminant Animals", paper presented at The 42nd Annual Conference of the American Association of Bovine Practitioners, 2009, 32 pages.

* cited by examiner

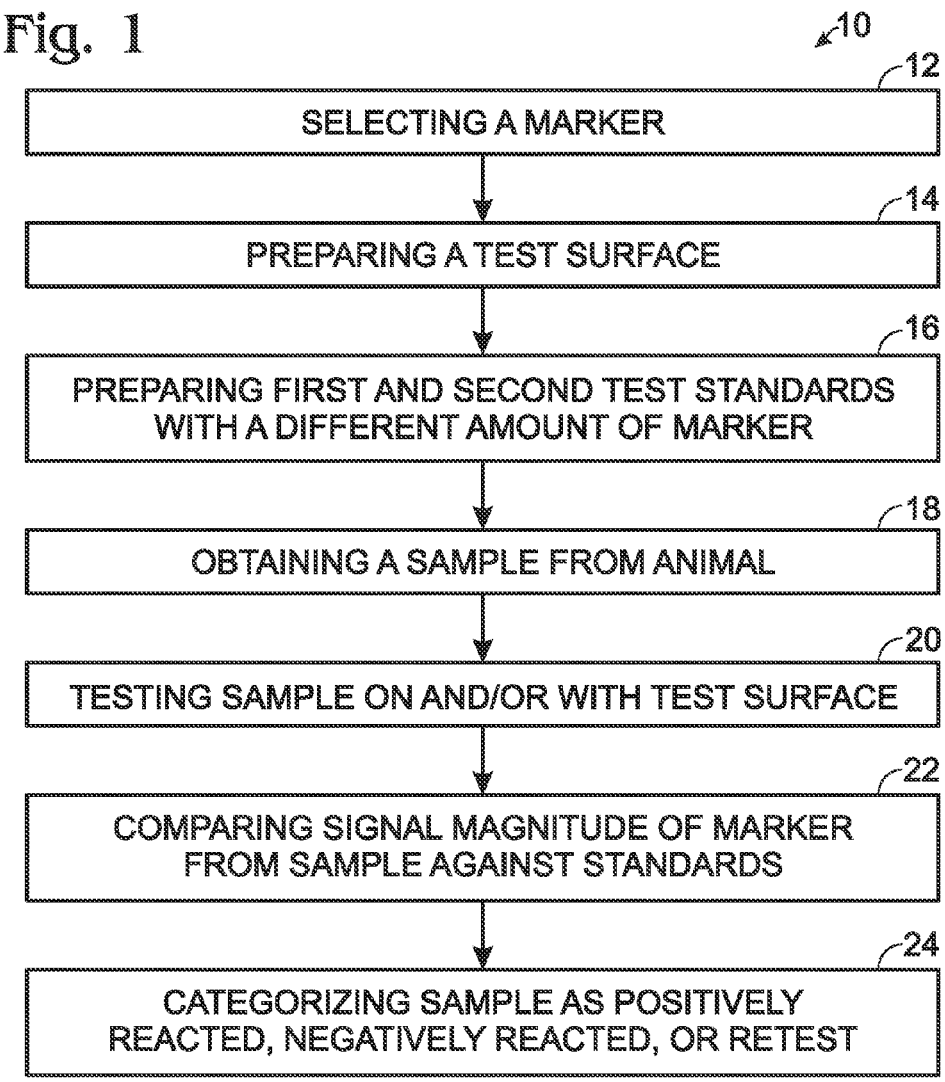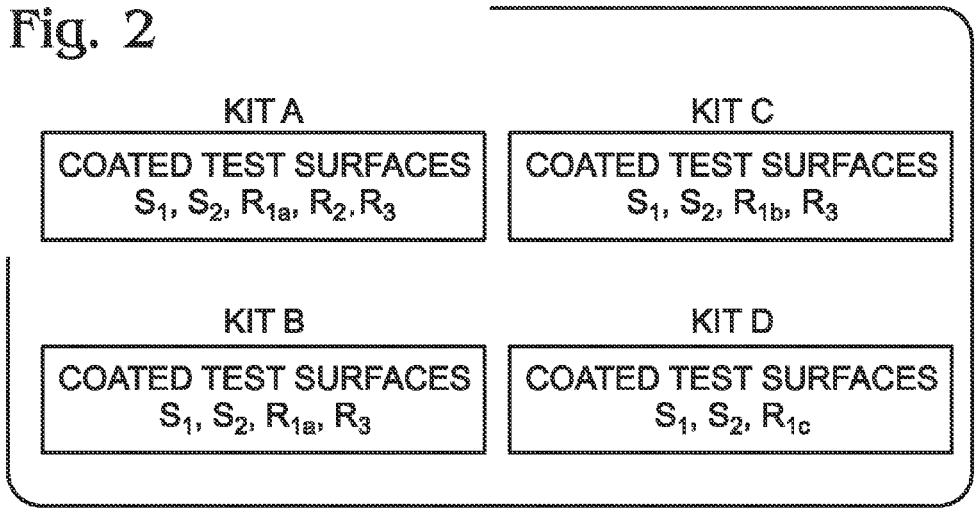

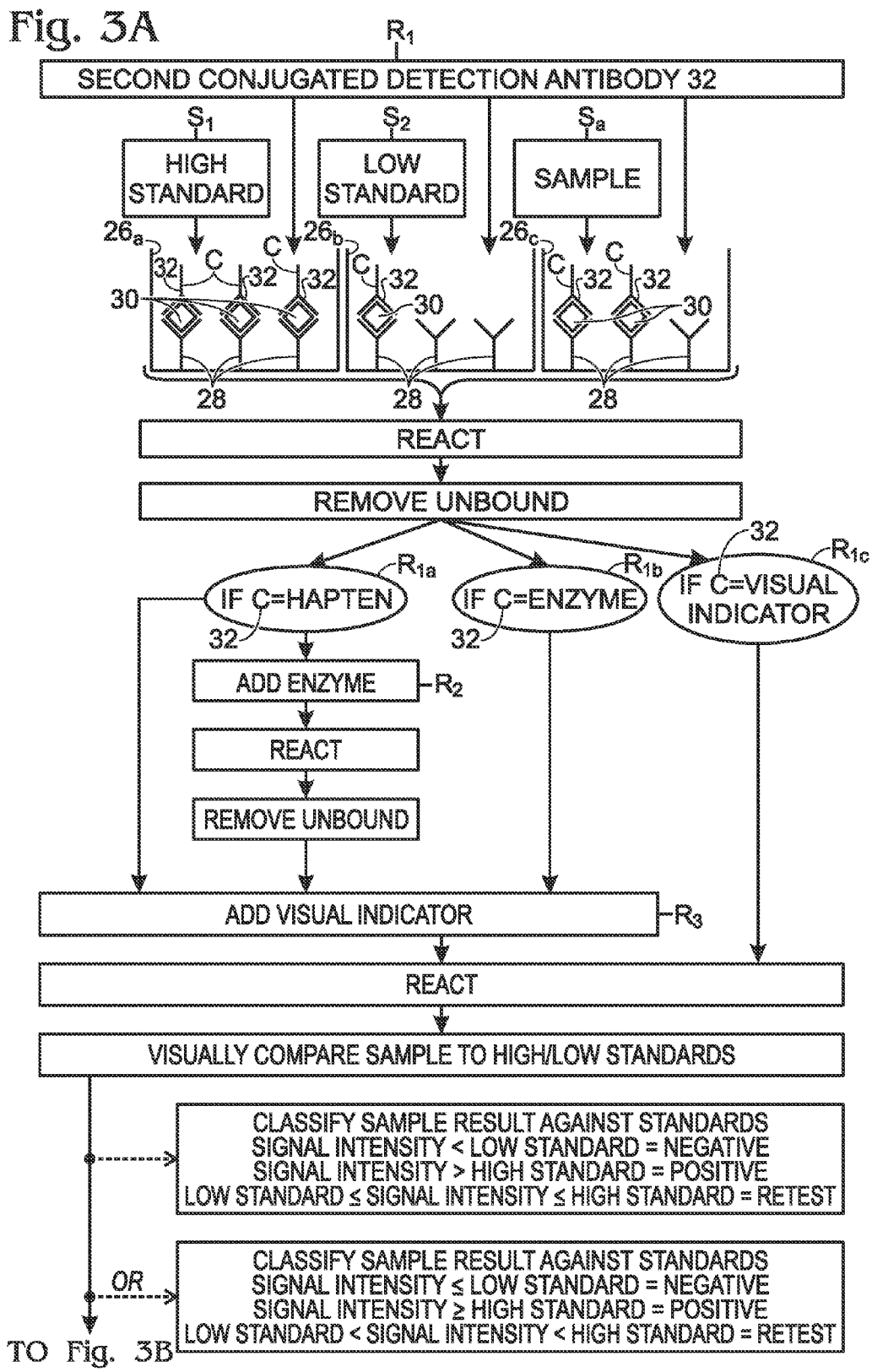

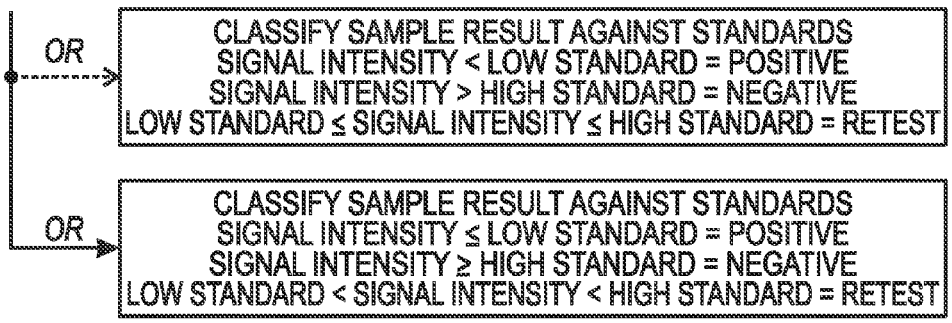
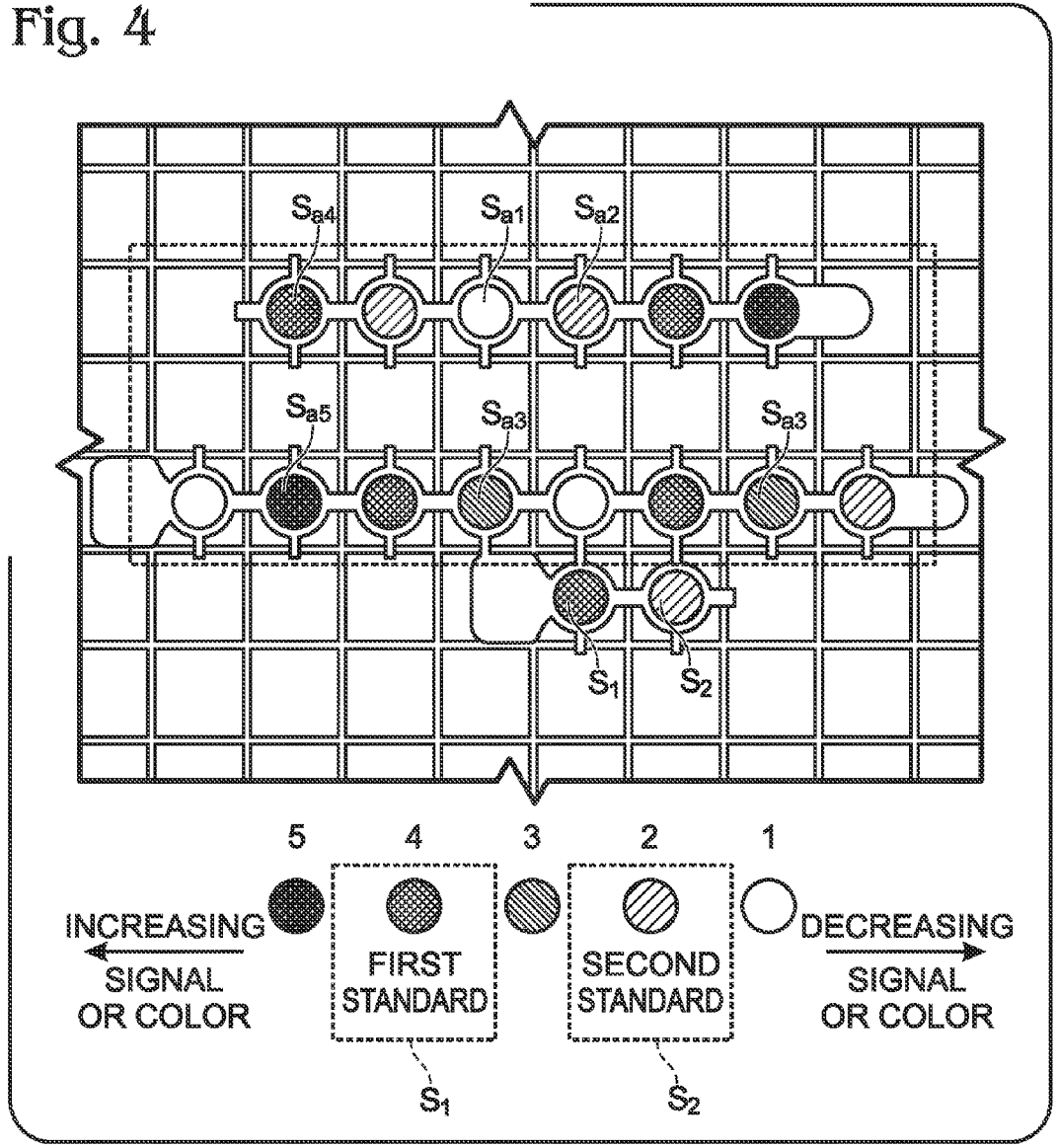

SYSTEMS AND METHODS FOR DETECTING ANIMAL PREGNANCY

BACKGROUND

The present disclosure relates generally to test systems and methods for detecting the presence of markers in animals. More specifically, the test systems and methods of the present disclosure may be used to detect a pregnancy marker that indicates if an animal, such as a ruminant, is pregnant.

Traditional testing for determining the pregnancy of some animals, such as ruminants, involves physical inspection of such an animal by a veterinarian. Traditional testing methods include using ultrasound and by rectal palpation. However, these tests require an expert to perform the test, are time intensive, and are not cost effective.

Blood-based or other body fluid-based (i.e., milk) tests for detecting pregnancy markers provide another tool for aiding in early pregnancy diagnosis. In such tests, a sample of animal fluid can be withdrawn onsite, and then sent to an offsite laboratory for detection of a marker whose presence indicates that an animal is pregnant. For example, BioTracking LLC offers a laboratory test service for detecting the presence of a protein marker called pregnancy-specific protein B (PSPB) in ruminant animals. See U.S. Pat. Nos. 4,554,256 and 4,705,748, both of which are incorporated herein by reference. This test requires sending a blood sample taken onsite from a ruminant, such as a cow, to a laboratory, where a sandwich ELISA test is used to detect the presence of PSPB in the sample using quantitative means. PSPB includes several molecular weight and isoelectric variants of proteins. (Sasser and Ruder, 1987 & Sasser et al., 1989). Therefore, a polyclonal antiserum can be used to detect several of these protein variants of PSPB (Sasser et al., 1986). Additionally, PSPB molecules, referred to as pregnancy associated glycoproteins (PAGs), have been found in several eutherian mammals (Placentalia); most specifically they have been found in Artiodactyla, Perissodactyla, Carnivora and Rodentia (Szafranska et al., 2006).

There is not currently available a simple, non-laboratory (i.e., "on-the-farm") test for detecting markers, such as a pregnancy marker, that a non-professional can fully administer in the field. A need exists for a test that employs qualitative or semi-qualitative metrics for detecting markers, including for detecting pregnancy markers to determine if an animal is pregnant. A non-professional could use such a test in the field instead of requiring a professional laboratory analysis. An onsite test may also improve temporal efficiency by decreasing the time from sample collection to result, potentially from several days to hours or minutes.

Moreover, testing methods designed only to render a binary determination (e.g., positive/negative; reactive/non-reactive; and/or pregnant/not-pregnant) are limited in that they produce ambiguous results under certain conditions. For example, when a pregnancy is aborted or terminates prematurely, certain pregnancy markers may still be present in the blood. Depending on the timing and method of detection used, these markers may be detected creating a false positive result (e.g., a not pregnant animal being categorized as pregnant). False positives are detrimental to reproductive management decisions as temporal efficiency is decreased (e.g., takes longer to correctly identify the pregnancy status of the animal).

When using a binary approach, a main way to improve and optimize test results is by adjusting the sensitivity and specificity of the test. For pregnancy testing, sensitivity may be the percentage of pregnant animals correctly identified as pregnant. Specificity may be the number of not pregnant animals correctly identified as not pregnant. The problem is the sensitivity and specificity for a binary classification is connected such that an improvement in one parameter can be offset by decreased performance in the other. For example, a cutoff that results in more efficient identification of not pregnant animals (improved specificity) can be offset by having more unintentional hormone induced abortions due to more false negatives (lower sensitivity). A cutoff resulting in better identification of pregnant animals (improved sensitivity) and less induced abortions can be offset by decreased efficiency for taking longer to identify a portion of not pregnant animals due to more false positives (lower specificity).

Under the binary approach, there is therefore some probability of false positives and false negatives no matter what signal is set as the binary test standard. Setting the test standard at a cutoff yielding 100% sensitivity will increase the probability of false positives. Setting the test standard cutoff to yield 100% specificity will increase the probability of false negatives. Setting a cutoff between 100% sensitivity and 100% specificity may allow for some optimization, but there will remain some probability of false positive and false negative results.

A need exists for a test that can minimize the issues associated with specificity and sensitivity for binary tests. A need exists for a pregnancy test for early identification of non-pregnant animals with limited misidentification of pregnant animals. The sooner a decision can be made following previous pregnancy and subsequent breeding, the more benefit is attained.

SUMMARY

The present disclosure may include systems and methods for detecting one or more markers. The marker being detected may be a pregnancy marker present in an animal when the animal is pregnant. The method may include selecting a marker, preparing a test surface for detecting the marker, preparing first and second test standards that may respectively correspond to a first amount of marker and second amount of marker different from the first amount of marker, obtaining a sample from the animal, testing the sample on the test surface, comparing the magnitude of a signal corresponding to the level of marker in the tested sample against the first and second standards, and categorizing the animal based on the tested sample, for example, as positive/reactive (e.g., pregnant), negative/non-reactive (e.g., not pregnant), or recheck. Recheck may indicate that another sample should be retrieved at a time after the initial sample was retrieved to determine a reading, for example, of positive/reactive (e.g., pregnant), negative/non-reactive (e.g., not pregnant), recheck again, etc.

A kit of the present disclosure may include one or more test surfaces coated with a biomolecular recognition element (e.g. a detection antibody or antigen, etc.) specific to the marker of the animal being detected, a first standard or control that may provide an indication consistent with a first amount of the detected marker found in a sample, a second test standard that may provide an indication consistent with a second amount of marker found in a sample, and one or more solutions with reagents for performing the test. The test kit may be provided to a tester for performing the test (e.g. pregnancy test) in the field to detect the marker in a sample of an animal.

BRIEF DESCRIPTION OF THE DRAWINGS

FIG. 1 is a flow chart illustrating a method of detecting and analyzing the presence of a marker in an animal according to the present disclosure.

FIG. 2 illustrates embodiments of testing kits of the present disclosure for detecting a marker that may each include one or more testing surfaces, one or more standards, and one or more reagents.

FIGS. 3 (a-b) are a flow chart illustrating embodiments of methods of detecting and analyzing the presence of a marker in an animal according to the present disclosure.

FIG. 4 shows an embodiment of an assay with test surfaces including a first standard of a marker, a second standard of the marker, and test samples from one or more animals to compare qualitatively against the first and second standards.

DETAILED DESCRIPTION

As shown in FIG. 1, the present disclosure may include a testing method 10 for detecting one or more markers. The marker being detected may be a pregnancy marker present in an animal when the animal is pregnant. The method may include selecting a marker 12, preparing a test surface for detecting the marker 14, preparing first and second test standards that may respectively correspond to a first amount of marker and second amount of marker different from the first amount of marker 16, obtaining a sample from the animal 18, testing the sample on and/or with the test surface 20, comparing the magnitude of a signal corresponding to the level of marker in the tested sample against the first and second standards 22, and categorizing the animal based on the tested sample, for example, as positive/reactive (e.g., pregnant), negative/non-reactive (e.g., not pregnant), or recheck. Recheck may indicate that another sample should be retrieved at a time after the initial sample was retrieved to determine a reading, for example, of positive/reactive (e.g., pregnant), negative/negative (e.g., not pregnant), recheck again, etc.

As shown in FIG. 2, the present disclosure may include a test kit, such as Kit A, Kit B, Kit C, and/or Kit D, for detecting one or more markers. The kit may include one or more test surfaces coated with a biomolecular recognition element (e.g., a detection antibody, antigen, etc.) specific to the marker of the animal being detected, a first standard or control $S_1$ that may provide an indication consistent with a first amount of the detected marker found in a sample, a second test standard $S_2$ that may provide an indication consistent with a second amount of marker found in a sample, and one or more solutions R (e.g., $R_{1a}$, $R_2$, $R_3$ for Kit A) with reagents for performing the test. The test kit may be provided to a tester for performing the test (e.g. pregnancy test) in the field to detect the marker in a sample of an animal.

The methods and systems (e.g., kits) of the present disclosure will be described in detail below. While the detection of pregnancy markers in animals is used as an illustrative example throughout, it will be appreciated that the systems and methods of the present disclosure can also be applied to detecting markers for other types of testing or diagnostic procedures, including testing animals for the presence of markers associated with caprine arthritic encephalitis (CAE), bovine viral diarrhea (BVD), etc.

Selection of Marker(s) to Detect

Using the methods and systems of the present disclosure, several types of markers can be detected. The marker being detected may indicate whether an animal is pregnant or has a particular disease or condition. The marker being detected may be a protein, a lipid, a carbohydrate, etc. The marker being detected may depend on the type of animal being tested, the disease, condition, etc. being tested, the format of the test (i.e., assay, strip, etc.), and/or the type of biomolecular recognition element (e.g. antibodies, antigens, etc.) being used to detect the marker. The marker being detected may be a single marker (e.g., a protein marker) or a combination of markers (e.g., a protein marker and a steroid marker; two different protein markers; two variants of the same protein marker, etc.). The marker being detected may be specific to one condition (e.g., pregnancy) or multiple conditions (e.g., pregnancy and a disease)

In some embodiments, the marker being detected, when present in increased or increasing amounts, may indicate a positive/reactive (e.g., pregnant) result. In some embodiments, the marker being detected, when absent or present in decreased or decreasing amounts, may indicate a positive/reactive (e.g., pregnant) result.

As an example, there are several pregnancy markers that may be detected to indicate if an animal is pregnant.

PROTEIN MARKERS: In some embodiments, a protein marker may be detected for determining pregnancy. The protein marker may be a protein from the aspartic acid protease family. The protein marker may be pregnancy specific protein B (PSPB) or any of the PSPB variants (see Sasser et al. (1987) that identifies about 42 variants), and/or any of the pregnancy-associated glycoprotein (PAG) molecules. Several variants of PAG are known, including PAG-1, PAG-2, PAG-3, PAG-4, PAG-5, PAG-6, PAG-7, PAG-9, PAG-16, PAG-18, PAG-19, PAG-55, and MON PAG (see U.S. Pat. Nos. 6,869,770; 7,393,696; and 7,575,861, all of which are incorporated by reference).

It is believed that all of the PAG variants may be molecular forms of PSPB. PSPB is a protein isolate (a mixture of proteins). PAG was termed at a later time than was PSPB, and some, many, or all of the individual PAG's may be present in the PSPB protein fraction (see Butler et al. 1982; Zoli et al. 1991; and Hughes et al. 2003).

PSPB and PAG's belong to a large family of aspartic peptidases expressed in the placenta of species in the Artiodactyla order (e.g., cow, sheep, goat, pig, bison, deer, elk, moose, bighorn sheep, mountain goat, camel and other wild ungulates (split hoofed)) (see Hughes et al., 2003). They are also found in the Perissodactyla order (e.g., horse) and Carnivora order (e.g., cat). Hence, the systems and methods of the present disclosure that employ PSPB and/or PAG can be used to detect the pregnancy of any of these animals, or any other animal in which PSPB and/or PAG is found.

In some embodiments, measuring the concentration of the protein marker found in a sample (e.g., blood, serum, plasma, etc.) retrieved from an animal may indicate whether the animal has a level of the protein marker in the sample consistent with being pregnant. For example, a concentration of PSPB that is less than or equal to between about 0.01 nanograms per milliliter (ng/ml) to about 1.0 ng/ml of PSPB in serum of an animal may indicate the animal is not pregnant. A concentration of PSPB that is more than or equal to between about 0.1 ng/ml to about 1.5 ng/ml of PSPB in serum of an animal may indicate the animal is pregnant.

To obtain an accurate pregnancy reading based on the selected marker, the sample may need to be retrieved from the animal at a specific time after conception or insemination. For example, on or after about 30 days after conception/insemination, a sample concentration equal to or below about 0.2 ng/ml of PSPB in ruminant serum may indicate the ruminant is not pregnant, and equal to or above about 0.4 ng/ml of PSPB in ruminant serum may indicate that the ruminant is pregnant. A level between about 0.2 ng/ml and about 0.4 ng/ml may indicate that the animal should be rechecked at a later time to determine if the animal is pregnant.

In some embodiments, depending on what form of PSPB/PAG is being detected, and what type of pregnancy marker detector (e.g., antibody) is being used for the detection, the sample may be withdrawn earlier than 30 days post-insemination. For example, some variants of PSPB/PAG have a different expression profile in the blood than other variants of PSPB/PAG, which may allow for accurate detection of pregnancy earlier than 30 days (see Sasser et al. (1986)).

Other protein markers that can be detected to determine pregnancy according to the present disclosure include bovine antigen glycoprotein (BAG); early pregnancy factor (EPF); early conception factor (ECF); pregnancy-specific glycoprotein (PSG60); pregnancy serum protein 60 (PSP-60); and/or any of the interferon stimulated gene proteins (ISGPs) and/or the interferon-tau induced proteins, which include myxovirus resistance genes (e.g. MX1), UCRP, ISG-15, ISG-17, GCP-2, 2',5'oligoadenylate synthetase 1 (OAS 1), beta 2-microglobulin, IRF-1, IRF-2, I-8U, 1-8D Leu-13/9-27, and COX-2 (see U.S. Patent App. No. 2008/0026384, which is incorporated herein by reference).

For example, MX1, MX2, Oas 1, and ISG-15 are interferon stimulated gene proteins that may be used as markers for detecting pregnancy. The proteins are produced in response to the presence of interferon tau, which is a product of the trophoblast. The presence of interferon tau may provide a signal to the maternal system that an embryo is in the uterus. The messenger RNA for MX and ISG15 may arise at about 15 days after conception and remain in cattle until about 30 days to about 40 days after conception. Ovine ISG15 mRNA may be detectable on about day 13 of pregnancy, peak around about day 15, and remain high through about day 19. The effect of interferon tau stimulation is to continue the presence of the MX or ISG-15 messenger RNA until about 35 days after conception. The interferon tau response described above is for ruminant animals (sheep, cows, goats, etc.). It is suggested that MX and ISG15 protein may be used to detect pregnancy in cows (and other ruminants such as sheep) and gilts (pigs). (Hicks et. al. 2003).

STEROID MARKERS: In some embodiments, a steroid marker such as progesterone or estrone sulfate may be detected for determining pregnancy. Progesterone is present during the pregnancy of all eutherian (placental) mammals and is required to maintain pregnancy. Progesterone is present during the reproductive cycle but is absent when the animal is in heat. If conception occurs, progesterone may remain high and not decline as it would at the end of a reproductive cycle and during heat. Accordingly, the amount of progesterone in the blood of an animal at the time of an expected next heat may be high if pregnant and low if not pregnant. The absence of progesterone in the blood may confirm non-pregnancy and/or that an animal is in heat.

For example, in some types of tests for cattle, a level at or below about 1 ng/ml to about 2 ng/ml of progesterone in serum may indicate that the animal is in, or near, heat and is not pregnant. A level at or above about 2 ng/ml to about 6 ng/ml of progesterone in serum may indicate the animal is pregnant. A level between about 1-2 ng/ml to about 2-4 ng/ml may indicate that the animal should be rechecked at a later time to determine if the animal is pregnant. Progesterone levels can be measured to determine the pregnancy of cattle about 18 to 24 days, and perhaps preferably 20 to 22 days, after conception/insemination.

In other embodiments, an estrogenic hormone such as estrone sulfate may be detected for determining pregnancy. Estrone sulfate is a pregnancy marker for several mammals that is produced by the fetal/placental unit and can be measured in, for example, a blood sample retrieved from the mother. This hormone is produced by the fetal/placental unit and does not arise until the late first to early second trimester of gestation. The level of estrone sulfate can be measured in cattle and horses, and in other animals, such as pigs, goats, sheep, alpaca, llama, etc., to determine pregnancy.

For example, in cows, the level of estrone sulfate increases during the period of gestation. On or after about 100 days of gestation, the level of estrone sulfate present in a cow may be measured to determine pregnancy. Accordingly, estrone sulfate levels can be measured to determine the pregnancy of cattle about 100 days after conception/insemination.

For horses, levels of estrone sulfate are different at different times of gestation. On or after about 70 days of gestation, the level of estrone sulfate in a horse can be measured to determine pregnancy. Accordingly, estrone sulfate levels can be measured to determine the pregnancy of horses about 70 days after conception/insemination.

In some embodiments, on or after about 35 days after conception/insemination, a level at or below about 5.0 ng/mL of estrone sulfate in serum may indicate the horse is not pregnant. On or after about 70 days after conception/insemination, a level at or below about 9.4 ng/ml of estrone sulfate in serum may indicate the horse is not pregnant. On or after about 70 days after conception/insemination, a level at or greater than about 13 ng/ml of estrone sulfate in serum may indicate the horse is pregnant. On or after about 70 days after conception/insemination, a level between about 9.5 ng/ml and about 13 ng/ml of estrone sulfate in serum may indicate that another sample should be retrieved from the horse at a later time after the initial sample was taken to determine pregnancy.

Selection of Biomolecular Recognition Elements Specific to Marker(s) being Detected An appropriate biomolecular recognition element (BRE) may be selected for use depending on the marker(s) being detected. Any BRE that is capable of allowing detection of a selected marker can be used. For example, the marker may be a molecule, receptor, antibody, antigen, nucleic acids, etc. The BRE may detect a combination of different markers (e.g., a protein marker and a carbohydrate marker, more than one protein marker, more than one variant of a marker, etc). BRE(s) specific to multiple markers of one disease or condition, or to different diseases or conditions, may be used in combination if desired.

In some embodiments, a preferred BRE may be a detection antibody. The detection antibody may be polyclonal or monoclonal. Accordingly, detection antibodies are used as an illustrative, example below for detecting markers. It will be appreciated that detection antibodies can be substituted in the discussion below with any other appropriate BRE capable of allowing detection of the marker being detected.

For example, when detecting the pregnancy marker of PSPB, the BRE may be a detection antibody selected that is specific to PSPB. The detection antibody may be, or include, polyclonal rabbit immunoglobulin (IgG), polyclonal goat IgG, polyclonal sheep IgG, polyclonal mouse IgG, monoclonal mouse or rabbit IgG, etc. In some embodiments, the detection antibody may detect either a single variant or multiple variants of PSPB/PAG.

Preparation of Test Surfaces for Conducting Test

There may be provided a test or support surface used for performing a test for detecting the presence of a selected marker(s). The test or support surface may be coated with/hold the selected detection antibodies, etc. specific to the marker(s) being detected.

The support surface may be any surface on which the selected detection antibodies, etc. can be coated/held for detection of the selected marker(s). In some embodiments, the test or support surface may be part of an assay having one or more containers (or wells). The test or support surface may be the inner surface of a well or container. The inner surface of one or more wells or containers may be coated with the detection antibody specific to the marker(s) being detected. For example, when detecting PSPB, each well or container of an assay may be coated with an antibody specific to PSPB. Each well or container may be pre-coated with the antibody before the coated well or container reaches the tester.

Any appropriate assay or ELISA (sandwich, indirect, competitive, reverse, etc.) can be provided. The assay provided may be a polystyrene microplate, having wells/containers with inner surfaces capable of being coated with antibody. These inner surfaces may or may not be treated with substances known in the art to promote or enhance coating. For example the surface can be a maxisorp, Polysorp®, medisorp, Minisorp® or Covalink® surface. Each well or container may have a total surface area of about 2.5 $cm^2$/well. Each well or container may have a total volume of about 350 µl/well. Each well or container may have a suggested working volume of about 250 µl/well. Each well or container may be white or opaque to allow for easier visualization of any color, or any visually detectable change, occurring in or on the well or container. It will be appreciated that the size, surface area, total and/or working volumes, appearance, and/or color/visual parameters and/or qualities can be modified as desired within the scope of the present disclosure. For example, the working volume for each well or container can be about 25 µl/well to about 250 µl/well within the scope of the present disclosure.

In some embodiments, the test or support surface may be part of a vial (or container or well), a test strip, a chromatography substrate, a gene chip, a Snap® test, or any other diagnostic test or test system used for detecting markers, such as pregnancy markers. The test or support surface may be made of paper, plastic, glass, metal, etc. and take several forms such as paddle, beads, wells, electrodes, etc.

In some embodiments, non-specific adsorption to the test surfaces coated with the BRE (e.g. the detection antibody), such as the coated well/container of an assay, may be minimized by blocking the test surface with a blocking agent. The blocking agent may be one or more proteins, sugars and/or polymers such as bovine serum albumin, gelatin, polyethylene glycol, sucrose, etc.

In some embodiments, the test surface coated with the BRE (e.g., the detection antibody), such as the coated well/container of an assay, may be coated with a preserving (or stabilizing) agent to preserve the activity of the test surface. Test surfaces coated with the BRE and the blocking agent may also be coated with the preserving agent. The preserving agent may allow the test surfaces coated with the preserving agent, and the BRE and/or blocking agent, to be stored for an extended period of time before use. Test surfaces coated with the preserving agent, and the BRE and/or blocking agent, may maintain immunological activity for several months compared to if no preserving agent is employed (where immunological activity of a test surface coated with the BRE and/or a blocking agent may continually decline over time).

The preserving agent may be composed of any organic or inorganic buffer with some or all of the following characteristics: a concentration between about 0.005 M and about 0.200 M, a pKa value between about 6.0 and about 8.0, high solubility, non-toxicity, limited effect on biochemical reactions, very low absorbance between about 240 nm and about 700 nm, enzymatic and hydrolytic stability, minimal changes due to temperature and concentration, limited effects due to ionic or salt composition of the solution, limited interaction with mineral cations, and/or limited permeability of biological membranes. Stabilization compounds may be any reducing or non-reducing carbohydrate in the range of concentrations (weight/volume or volume/volume) from about 0.005% to about 20%.

Preparation of Test Standards

There may be provided one or more test standards corresponding to one or more fixed levels of the marker being detected. In some embodiments, a first test standard and a second test standard may be provided. To set the standard levels, the first test standard may correspond to a first amount of the marker being detected. The second test standard may correspond to a second level of the marker being detected, which is a different level from the first amount.

When a pregnancy marker is being detected, each standard may correspond to a different fixed level of the pregnancy marker. The first or high standard may correspond to the minimum level of the pregnancy marker found in a pregnant animal. The second or low standard may correspond to the maximum level of the pregnancy marker found in a non-pregnant animal. The pregnancy marker used for the test standard(s) may be a purified, semi-purified or complex form of the marker of the species under test or be from a species in which the cross-species of the marker can be used to set an accurate cutoff level for pregnancy status determination.

For example, when the pregnancy marker being detected is PSPB, the high standard may correspond to the level of PSPB corresponding to a minimum level of PSPB present in a pregnant animal. The high standard for a ruminant may correspond to a concentration between about 0.01 ng/ml and about 1.0 ng/ml of PSPB in serum. The low standard may correspond to the level of PSPB corresponding to the maximum level of PSPB present in a not pregnant animal. The low standard for a ruminant may correspond to a concentration between about 0.2 ng/ml and about 0.4 ng/ml of PSPB in serum.

The high and low standards can be determined in a similar manner for whatever pregnancy marker is being detected. For example, when progesterone is the pregnancy marker for a cow, then the high standard may be about 2 ng/ml to 6 ng/ml of progesterone in serum and the low standard may be about 1 ng/ml to 2 ng/ml of progesterone in serum. When estrone sulfate is the pregnancy marker for a horse, then the high standard may be about 13 ng/ml of estrone sulfate in serum and the low standard may be about 9.4 ng/ml of estrone sulfate in serum.

The one or more test standard(s) may be provided to a tester in multiple ways. In some embodiments, a test kit, such as those in FIG. 2, may be provided to the tester. The kit may include a reagent solution of the high standard $S_1$ and of the low standard $S_2$. The high and low standard solutions may include fixed levels of the marker being detected, as described above. The high and low test standards may also be prepared from any solution that can generate a signal (visual or otherwise) consistent respectively with a positive/reactive (e.g. pregnant) level and a negative/non-reactive (e.g., not pregnant) level of the marker(s) being detected.

For an assay test, the high standard solution may be added to a first well or container of the assay and the low standard solution to a second well or container. Samples may then be tested in other wells or containers of the assay and compared against the low and high standards. In this way, the sample being tested may be compared in a similar testing environment (i.e., temperature, timing, preparation, etc.) as the standards, which may generate more accurate results.

In some embodiments, the high and low test standards may be prepared and provided to the tester in a ready-to-use condition for testing analysis. For example, when an assay is provided for performing the test, the high and low standards may be prepared and sealed in the first and second well or containers. A piece of paper may be included in the kit imprinted with signals (visual or otherwise) indicating the high and low standards levels. For example, a card may have color intensities imprinted on the card corresponding to the high and low standards, and the sample color intensity can be compared to the cards. Containers or vials may be provided with the high and low standards already prepared for comparison to the tested samples.

It will be appreciated that any of the above test standards can be provided in lieu of, or in addition to, the other test standards.

Obtaining Sample(s) from Animal(s)

The type of sample retrieved from the animal may depend on the marker being detected. The sample may be a blood sample, such as of whole blood, plasma, or serum. The sample may be of a biological or bodily fluid, such as of saliva, reproductive tract secretions (i.e., vulva, vaginal, uterine, cervical, oviductal, etc.), and/or ectodermal or skin origin secretions (e.g., tears, sweat, milk, urine, etc.). The sample may be of a tissue, a cell, and/or any biological solid. The sample may be an extract of any of the above. The sample may be a combination of any of the above.

Samples may be obtained from an animal using known retrieval procedures specific to the type of sample being taken. The time period in which the sample may be retrieved before testing may depend on the type of sample being obtained, the marker being detected, and/or the type of analysis or diagnosis being performed. The time period in which the sample should be tested after being retrieved may depend on the type of sample taken, the marker being detected, and/or the type of analysis or diagnosis being performed.

For example, when detecting a pregnancy marker, one or more samples may be retrieved from the tested animal after insemination of the animal. The time period for retrieving the sample may depend on the type of animal being tested, the pregnancy marker(s) being detected (e.g., different markers appear at different stages of gestation in different detectable amounts), and/or the BREs being used to detect the pregnancy marker (e.g., an antibody selected could detect different variants of pregnancy markers that appear at different stages of gestation in different detectable amounts).

As examples, in some embodiments, when detecting pregnancy of a ruminant using PSPB as the marker, the sample may be retrieved about 30 days or later after conception/insemination. When detecting pregnancy of a cow using estrone sulfate as the marker, the sample may be retrieved about 100 days or later after conception/insemination. When detecting pregnancy of a horse using estrone sulfate as the marker, the sample may be retrieved about 70 days or later after conception/insemination. When detecting pregnancy of a cow using progesterone as the marker, the sample may be retrieved about 18 to about 24 days after conception/insemination. The day of retrieving a sample can vary by species and may be near the time of expected heat if the animal has not conceived.

Testing Sample on Test Surface and Signal Development for Analysis

To detect if a marker is present in a sample, a signal from the sample may be compared against the signals of a high standard and a low standard. A qualitative/visual signal may be generated or visualized of the sample and test standards for making the comparison. The visual indicator may visualize or generate a signal of the sample and standards having a magnitude corresponding to the level of the marker present. The visual indicator may visualize or generate a signal for the first standard consistent with a first level of marker. The visual indicator may visualize a signal for the second standard consistent with a second level of marker.

For example, when detecting a pregnancy marker, the visual indicator may visualize for the high standard a signal consistent with a level, such as the minimum level, of the pregnancy marker found in a pregnant animal. The visual indicator may visualize for the low standard a signal consistent with a level, such as the maximum level, of the pregnancy marker found in a not-pregnant animal. The magnitude of the signal from an animal sample generated by the visual indicator may be compared against the standards to determine pregnancy.

Generating the visually detectable signal can be accomplished in several ways. Any visual indicator, including any dye, chromogen, substance, substrate, or solution capable of producing a qualitative indication or visually detectable change may be utilized. The generated signal may be visually detectable with or without special equipment. For example, the signal may be a color change, or the generation of a color change along a spectrum, that is visible without special equipment. In some embodiments, it is possible to detect changes in light absorbance visually, with non-specialized light detection equipment, or specialized equipment (e.g., Spectrophotometer). In some embodiments, the signal may be detected by measuring a change in a physical or chemical property of the substrate being tested based on the presence of a label, such as an enzyme label. Types of enzyme-labeled signals known to the art include: light absorbance, light emission, fluorescence, electrochemical signal, pH, etc.

As an example, FIG. 3 schematically illustrates embodiments of the present disclosure for generating a visually detectable signal of the substrate being tested. As shown in FIG. 3, test surfaces 26a, 26b, and 26c may each be coated with a first antibody 28 specific to the marker 30 being detected. As shown in FIG. 4, which is discussed later, the coated test surfaces may be the inner surfaces of the wells or containers of an assay, such as a sandwich ELISA.

Returning again to FIG. 3, a high standard or control $S_1$ may be exposed (also referred to as introduced) to test surface 26a, a low standard or control $S_2$ may be exposed to test surface 26b, and a sample $S_a$ may be exposed to test surface 26c. Each may be exposed to test surfaces 26a, 26b, 26c under a substantially constant pressure and temperature, and for substantially the same time period. Each may be first exposed to test surfaces 26a, 26b, 26c at substantially the same time. During the exposure period, any marker 30 present in the standards and sample may react and bind with the first detection antibody 28 coated on each test surface. At the conclusion of the exposure period, unbound standard or sample may be removed and discarded from each test surface.

The marker remaining bound to test surfaces 26a, 26b, 26c may be consistent with the level of marker present in the standards and sample. The more marker bound to the test surfaces, the more marker was present.

A signal corresponding to the bound marker may be visualized. The generation of a signal from the bound marker may be accomplished by exposing to each surface 26a, 26b, 26c a second detection antibody 32 specific to the marker 30 being detected. The second detection antibody 32 may be the same as, or different from, the first detection antibody 28. The second detection antibody 32 may be conjugated or labeled (as indicated with a C in FIG. 3.). The second detection antibody 32 may be conjugated or labeled by the tester or before being provided to the tester. A conjugated or labeled second detection antibody may be provided to the tester in a reagent solution $R_1$.

The second detection antibody 32 (or conjugated second detection antibody) may be exposed to test surfaces 26a, 26b, 26c under a substantially constant pressure and temperature, and for substantially the same time period. The second detection antibody 32 (or conjugated second detection antibody) may be first exposed to test surfaces 26a, 26b, 26c at substantially the same time. The second detection antibody 32 (or conjugated second detection antibody) may be exposed to test surfaces 26a, 26b, 26c before, at the same time as, and/or after the sample and standards are exposed to test surfaces 26a, 26b, 26c. During the exposure period, the second detection antibody 32 (or conjugated second detection antibody) may react with and bind to the marker 30 bound on each surface 26a, 26b, 26c. At the conclusion of the exposure period, unbound second detection antibody 32 (or conjugated second detection antibody) may be removed and discarded from test surfaces 26a, 26b, 26c.

The amount of second detection antibody 32 (or conjugated second detection antibody) bound to test surfaces 26a, 26b, 26c may be consistent with the level of marker 30 bound to each test surface. The more second detection antibody 32 (or conjugated second detection antibody) bound to each surface, the more marker 30 was bound to each surface.

To generate a visually detectable signal, the second detection antibody 32 (or conjugated second detection antibody) may be labeled or unlabeled. If labeled, then the conjugated or labeled second detection antibody 32 may generate a visually detectable signal upon binding to the marker 30 on each test surface. If unlabeled, then additional or secondary steps may be needed to label the second detection antibody 32 (or conjugated second detection antibody) to generate a visually detectable signal.

FIG. 3 illustrates several examples of generating a visually detectable signal of the second detection antibody 32 (or conjugated second detection antibody) bound to each test surface, which are discussed below.

a. Signal Development (if Conjugate (C)=Hapten): Hapten-Enzyme-Visual Indicator

In some embodiments, the second detection antibody 32 may be conjugated with a hapten, such as a small molecule. The hapten conjugated antibody may act as a detector that detects the molecule of interest. The hapten may be biotin, digoxigenin, dinitrophenol, fluroscein, etc. The second detection antibody conjugated with the hapten may be exposed to the bound marker 30 on each test surface 26a, 26b, 26c as described above. Unbound second detection antibody conjugated with the hapten may be removed and discarded from the test surfaces 26a, 26b, 26c, as described above.

An enzyme may be exposed to each test surface that may react with and/or bind to a hapten-conjugated detection antibody. The enzyme may be horseradish peroxidase, alkaline phosphatase, beta-galactosidase, or any enzyme capable of reacting with and/or binding to a hapten-conjugated antibody. The enzyme may be exposed to test surfaces 26a, 26b, 26c under a substantially constant pressure and temperature, and for substantially the same time period. The enzyme may be first exposed to test surfaces 26a, 26b, 26c at substantially the same time. During the exposure period, the enzyme may react with and/or bind to the hapten-conjugated second detection antibody 32 bound on each surface 26a, 26b, 26c. At the conclusion of the exposure period, unbound enzyme may be removed and discarded from test surfaces 26a, 26b, 26c.

A visual indicator may be exposed to each test surface that may react with and/or bind to the selected enzyme. The visual indicator may generate a signal whose magnitude corresponds to the amount of enzyme bound to each test surface. In some embodiments, the visual indicator may be an enzyme substrate (e.g., 3,3',5,5' tetramethylbenzidine (TMB)) specific to the selected enzyme (e.g., horseradish peroxidase). Any appropriate visual indicator can be used, such as TMB, fluroscein, etc. Other visual signal indicators may include X-gal, para-aminophenol, BCIP, p-nitrophenol, luminol, etc.

The visual indicator may be exposed to test surfaces 26a, 26b, 26c under a substantially constant pressure and temperature, and for substantially the same time period. The visual indicator may be first exposed to test surfaces 26a, 26b, 26c at substantially the same time. During the exposure period, the visual indicator may react with and/or bind to the enzyme bound to each surface 26a, 26b, 26c. The reaction may generate a visually detectable change or signal. The respective magnitude of the change or signal may correspond to the amount of marker 30 bound to each test surface 26a, 26b, 26c. At the specified time after the reaction begins, the signal may be detected and/or observed with or without stopping the reaction.

In some embodiments, a hapten reactive molecule labeled with an enzyme (e.g. avidin-peroxidase, anti-digoxigenin-peroxidase) may be exposed to each test surface that may react with and/or bind to a hapten-conjugated detection antibody. The hapten reactive molecule may be labeled with horseradish peroxidase, alkaline phosphatase, beta-galactosidase, or any enzyme capable of reacting with and/or binding to a hapten-conjugated antibody. The enzyme may be exposed to test surfaces 26a, 26b, 26c under a substantially constant pressure and temperature, and for substantially the same time period. The enzyme may be first exposed to test surfaces 26a, 26b, 26c at substantially the same time. During the exposure period, the enzyme may react with and/or bind to the hapten-conjugated second detection antibody 32 bound on each surface 26a, 26b, 26c. At the conclusion of the exposure period, unbound enzyme may be removed and discarded from test surfaces 26a, 26b, 26c. The labeling with streptavidin-horseradish peroxidase and/or avidin-horseradish peroxidase may act as an enhancer that enhances the visibility of the visually detectable color or signal. An enhancer, such as strepavidin conjugated with horseradish peroxidase (SA-HRP) and detected with 3,3',5,5'-Tetramethylbenzidine (TMB), or stepavidin conjugated with alkaline phosphatase (SA-AP) and detected with p-nitrophenyl phosphate (pNPP), can be used as appropriate with any of the other embodiments disclosed in or within the scope of the present disclosure.

As shown in FIG. 2, the reagents and components necessary to perform the test may be provided as Kit A. Kit A may include the test surfaces coated with the first detection antibody specific to the marker being detected, a bottle of reagent solution with high standard $S_1$, a bottle of reagent solution with low standard $S_2$, a bottle of reagent solution $R_{1a}$ with the hapten-conjugated second detection antibody, a bottle of reagent solution $R_2$ with an enzyme, and a bottle of reagent solution $R_3$ with the visual indicator.

b. Signal Development (if Conjugate (C)=Hapten): Hapten-Visual Indicator

The second detection antibody 32 conjugated with the hapten may be exposed to the bound marker 30 on each test surface 26a, 26b, 26c as described above. Unbound second detection antibody conjugated with the hapten may be removed and discarded from the test surfaces 26a, 26b, 26c, as described above.

A visual indicator may be exposed to the hapten-conjugated second detection antibody bound to each test surface 26a, 26b, 26c. The visual indicator (e.g., TMB) may be any that is capable of reacting with and/or binding to a hapten-conjugated detection antibody in a manner that generates a visually detectable change or signal. The visual indicator may generate a change or signal whose magnitude corresponds to the amount of hapten-conjugated second detection antibody bound to each surface 26a, 26b, 26c.

The visual indicator may be exposed to test surfaces 26a, 26b, 26c under a substantially constant pressure and temperature, and for substantially the same time period. The visual indicator may be first exposed to test surfaces 26a, 26b, 26c at substantially the same time. During the exposure period, the visual indicator may react with and/or bind to the hapten-conjugated second detection antibody 32 bound to each surface 26a, 26b, 26c. The reaction may generate a visually detectable change or signal. The respective magnitude of the change or signal may correspond to the amount of marker 30 bound to each test surface 26a, 26b, 26c. At the specified time after the reaction begins, the signal may be detected and/or observed with or without stopping the reaction.

As shown in FIG. 2, the reagents and components necessary to perform the test may be provided as Kit B. Kit B may include the test surfaces coated with the first detection antibody specific to the marker being detected, a bottle of reagent solution with high standard $S_1$, a bottle of reagent solution with low standard $S_2$, a bottle of reagent solution $R_{1a}$ with the hapten-conjugated second detection antibody, and a bottle of reagent solution $R_3$ with the visual indicator.

c. Signal Development (if Conjugate (C)=Enzyme): Enzyme-Visual Indicator

As shown in FIG. 3, in some embodiments, the second detection antibody 32 may be conjugated with an enzyme. The enzyme may be horseradish peroxidase, alkaline phosphatase, or any enzyme capable of reacting with and/or binding to marker 30.

The second detection antibody 32 conjugated with the enzyme may be exposed to the bound marker 30 on each test surface 26a, 26b, 26c as described above. Unbound second detection antibody conjugated with the enzyme may be removed and discarded from the test surfaces 26a, 26b, 26c, as described above.

A visual indicator may be exposed to each test surface 26a, 26b, 26c that reacts with and/or binds to the enzyme-conjugated second detection antibody bound to each test surface. The visual indicator (e.g., TMB) may be any that is capable of reacting with and/or binding to an enzyme-conjugated detection antibody in a manner that generates a visually detectable change or signal. The visual indicator may generate a change or signal whose magnitude corresponds to the amount of enzyme-conjugated second detection antibody bound to each surface 26a, 26b, 26c.

The visual indicator may be exposed to test surfaces 26a, 26b, 26c under a substantially constant pressure and temperature, and for substantially the same time period. The visual indicator may be first exposed to test surfaces 26a, 26b, 26c at substantially the same time. During the exposure period, the visual indicator may react with and/or bind to the enzyme-conjugated second detection antibody bound to each surface 26a, 26b, 26c. The reaction may generate a visually detectable change or signal. The respective magnitude of the change or signal may correspond to the amount of marker 30 bound to each test surface 26a, 26b, 26c. At the specified time after the reaction begins, the signal may be detected and/or observed with or without stopping the reaction.

As shown in FIG. 2, the reagents and components necessary to perform the test may be provided as Kit C. Kit C may include the test surfaces coated with the first detection antibody specific to the marker being detected, a bottle of reagent solution with high standard $S_1$, a bottle of reagent solution with low standard $S_2$, a bottle of reagent solution $R_{1b}$ with the enzyme-conjugated second detection antibody, and a bottle of reagent solution $R_3$ with the visual indicator.

d. Signal Development (if Conjugate (C)=Visual Indicator): Visual Indicator

As shown in FIG. 3, in some embodiments, the second detection antibody 32 may be labeled or conjugated with the visual indicator. The visual indicator may be any capable of producing a visually detectable change or signal with or without special equipment. For example, the visual indicator may be an enzyme substrate that produces fluorescence that can be detected by excitation using a light source. If the visual indicator is a fluorescent marker, such as fluroscein, the signal may be developed using light excitation of the fluorophore. Fluorescent signal detection may be accomplished by measuring the light emitted from the excited fluorophore visually or with a light reader. The light reader may have a filter that is specific to the emitted wavelength of the fluorophore being detected.

The second detection antibody 32 conjugated with the visual indicator may be exposed to each surface 26a, 26b, 26c. The visual indicator-conjugated second detection antibody 32 may be exposed to test surfaces 26a, 26b, 26c under a substantially constant pressure and temperature, and for substantially the same time period. The visual indicator-conjugated second detection antibody 32 may be first exposed to test surfaces 26a, 26b, 26c at substantially the same time. During the exposure period, the visual indicator-conjugated second detection antibody 32 may react with and/or bind to the marker bound to each surface 26a, 26b, 26c. The reaction may generate a visually detectable change or signal. The respective magnitude of the change or signal may correspond to the amount of marker 30 bound to each test surface 26a, 26b, 26c. At the specified time after the reaction begins, the signal may be detected and/or observed with or without stopping the reaction.

As shown in FIG. 2, the reagents and components necessary to perform the test may be provided as Kit D. Kit D may include the test surfaces coated with the first detection antibody specific to the marker being detected, a bottle of reagent solution with high standard $S_1$, a bottle of reagent solution with low standard $S_2$, a bottle of reagent solution $R_{1c}$ with the visual indicator-conjugated second detection antibody.

e. Signal Development—Others

Several other visual indicators, and/or systems and methods, can be utilized to generate a visually detectable signal within the scope of the present disclosure. For example, any molecule capable of acting as a visual indicator may be used for signal development. The visual indicator may be or include fluorophors, lumiphors, upconverting phosphors, dyes, chemiluminescent molecules, electrochemiluminescent molecules, etc. These may be free, bound, conjugated to, or encapsulated in nanoparticles. Other detection agents may be or include gold nanoparticles, silicon oxide nanoparticles, fluorescent nanoparticles; latex or other particles; etc. Other ways to generate a visual response may include using an enzyme-linked coagulation assay (see U.S. Pat. No. 4,668, 621); and/or an enzyme-linked precipitation assay. Other ways to generate a visual response may include generating a detectable electrical signal or refraction, such as by using enzyme-linked amperometry.

As one example, a lateral flow strip or filter pad may include testing surfaces coated with antibodies specific to the marker being detected. The high and low test standards may be exposed to a first and second portion of the test surface. The standard may be exposed to a third portion of the test surface. As described above, any marker present in the sample and/or standards may be bound to the test surface. Unbound sample and standards may be removed from the test surface. As described above, a second detection antibody specific to the marker being detected may be exposed and react with and/or bind to the marker bound on the test surface. In some embodiments, unbound second detection antibody may be discarded.

A visual indicator, such as a fluorescent nanoparticle, may be used for visualizing the presence of the marker being detected on the test surface. A fluorescent intensity may be created by excitation from a light source. A handheld reader of fluorescent intensity may be used to observe the signal from the excitation. The magnitude of the fluorescent intensity may correspond with the level of second detection antibody bound to the marker on the test surface of the strip or pad. The magnitude of the signal from the sample may be compared against the test standards on the test surface. Additionally, or alternatively, the strip or pad may include an indication of intensities corresponding to the low and high standards. An intensity visual discrimination card with indications corresponding to the high and low standards may also be provided.

Analysis of Visually Generated Signal of Sample Against Standards

As illustrated in FIG. 3, the visual indicator may give an indication regarding the presence of the marker in the sample.

In some embodiments, the first (or high) standard may correspond to a greater magnitude of signal strength of the marker than does the second (or low) standard. The stronger the magnitude of the signal, the higher the amount of marker that may be present in the sample. As such, if the magnitude of the sample signal is above (and in some cases equal to) the first (or high) standard, then that may indicate the sample is positive or reactive. If the magnitude of the sample signal is below (and in some cases equal to) the second (or low) standard, than that may indicate the sample is negative or non-reactive. If the magnitude of the sample signal is between the standards (and in some cases equal to the first standard and/or second standard), then that may indicate the animal whose sample is being tested should be rechecked or retested. A recheck or retest may indicate that another sample should be retrieved from the animal for analysis at some time after the initial sample was retrieved from the animal for analysis. The later sample can be checked against the standards as above. For example, a sandwich ELISA may be configured for this type of analysis, and there are various other testing systems that can be configured for this type of analysis within the scope of the present disclosure.

In some embodiments, a greater amount of marker that may be present in the sample may result in a decrease in the magnitude of the signal. As such, if the magnitude of the sample signal is below (and in some cases equal to) the first (or high) standard, then that may indicate the sample is positive or reactive. If the magnitude of the sample signal is above (and in some cases equal to) the second (or low) standard, than that may indicate the sample is negative or non-reactive. If the magnitude of the sample signal is between the standards (and in some cases equal to the first standard and/or second standard), then that may indicate the animal whose sample is being tested should be rechecked or retested. A recheck or retest may indicate that another sample should be taken from the animal for analysis at some time after the initial sample was taken from the animal for analysis. The later sample can be checked against the standards as above. For example, a competitive and/or substitute ELISA may be configured for this type of analysis, and there are various other testing systems that can be configured for this type of analysis within the scope of the present disclosure.

FIG. 4 is an example of signal analysis using the systems and methods of the present disclosure. As shown in FIG. 4, there may exist a spectrum of magnitude of reactivity level from 1 (low) to 5 (high). The first standard $S_1$ may be the high standard and correspond to a reactivity of 4 and the second standard $S_2$ may be the low standard and correspond to a reactivity of 2. The signals of samples $S_a$ may then be compared against standards $S_1$ and $S_2$. In this example, samples $S_a$ whose signal magnitude is at or above the high standard, such as $S_{a4}$ or $S_{a5}$, may be considered positive or reactive. Samples $S_a$ at or below the low standard, such as $S_{a1}$ or $S_{a2}$, may be considered negative or non-reactive. Samples $S_a$ between the standards, such as $S_{a3}$, may be considered rechecks. In some embodiments, samples equaling the high standard (e.g. $S_{a4}$) and/or low standard (e.g. $S_{a2}$) may instead be classified as a recheck.

In some embodiments, the first standard $S_1$ may be the low standard and correspond to a reactivity of 4 and the second standard $S_2$ may be the high standard and correspond to a reactivity of 2. The signals of samples $S_a$ may then be compared against standards $S_1$ and $S_2$. In this example, samples $S_a$ whose signal magnitude is at or above the low standard, such as $S_{a4}$ or $S_{a5}$, may be considered negative or non-reactive. Samples $S_a$ at or below the high standard, such as $S_{a1}$ or $S_{a2}$, may be considered positive or reactive. Samples $S_a$ between the standards, such as $S_{a3}$, may be considered rechecks. In some embodiments, samples equaling the low standard (e.g. $S_{a4}$) and/or high standard (e.g. $S_{a2}$) may instead be classified as a recheck.

It will also be appreciated that the samples $S_a$ shown in FIG. 4 may all be from the same animal, or from different animals. The samples $S_a$ may be a first sample of an animal (e.g. $S_{a3}$) and a rechecked sample of an animal (e.g. $S_{a1}$ or $S_{a5}$) retrieved at some time period after the first sample was retrieved.

Each magnitude 1 through 5 shown in FIG. 4 may correspond to different colors or to different levels of intensity along a spectrum for one color (e.g., from 1 low to 5 high). Each magnitude 1 through 5 may correspond to a mixture of color intensities of one or more different colors. Each magnitude 1 through 5 may correspond to a signal other than a color, such as a visually detectable signal.

FIG. 4 may represent the results of an assay test for detecting the presence of a pregnancy marker (e.g. PSPB) in an animal sample to determine pregnancy. The magnitude of the signal may represent magnitudes of a color, such as blue, that is present when the pregnancy marker may be present. The darker the color, the more pregnancy marker may be present. (As noted above, in some embodiments, this may be reversed such that the darker/higher the color intensity, the less pregnancy marker may be present). The high test standard may be an intensity of blue color consistent with the level of the pregnancy marker found in a pregnant animal. The low test standard may be an intensity of blue color consistent with a level of the pregnancy marker found in a not pregnant animal.

A qualitative, visual analysis may be performed to compare a sample in an assay well against the high and low test standards in other assay wells to determine if an animal is pregnant (equals blue color intensity same or above high standard), not pregnant (equals blue color intensity same or below low standard), or recheck (equals blue sample color intensity between standards). Another sample can then be retrieved from the animal for analysis within a few days, perhaps within 7 days, if testing a ruminant, after the first sample was retrieved that indicated a recheck.

In some embodiments, the use of an enhancer, such as those above, may be used to increase the intensity of the signal or color to give an increase in the spread or dynamic range between the first and second standards. As an illustrative example, on an intensity scale, the lightest color may be a 1 and the darkest color may be a 2, with a dynamic range between the colors of about 1 to 2. Use of the enhancer may increase the darkest color from 2 to 20 resulting in a dynamic range of 1 to 20, which is a 10-fold increase in the dynamic range. Use of the enhancer may therefore increase the intensity of the response for the high and low standards as well. The overall effect may be to give a better separation between the low standard and the high standard. This better separation may allow for a tester to determine even more easily whether a test sample is considered a positive, negative, or recheck by comparing via a visual or qualitative analysis the signal of the sample against the standards.

Other Advantages of the Systems and Methods of the Present Disclosure

The disadvantages of a binary test using blood-based markers is the tradeoff between sensitivity and specificity of the test depending upon the selected cutoff level for the measured marker. This is an issue. For example, PSPB residual protein from a dead embryo may give a positive test when in fact there is no pregnancy. Also, usually loss of an embryo early in gestation, 30 to 80 days, can present results as a positive test when in fact the cow is not pregnant.

Employing a three-result visual test (positive/reactive, negative/non-reactive, recheck) may avoid the sensitivity and specificity issues associated with a two-result binary (positive, negative) test. For example, unlike in a binary test, a high sensitivity can be maintained for a three-part test while the inefficiency of lost specificity may be minimized by placing some or all potentially false positive, false negative and/or marginal/ambiguous result yields of a binary test into a recheck category. A sample categorized as recheck allows another sample to be taken at a later time, which may allow for correct identification (positive or negative) in the later test in a minimum amount of time.

Specifically for pregnancy testing in animals, the recheck category may improve management decision making. Normally, animals classified as pregnant will have a confirmation test up four to six weeks or more after the first test. If a binary test yields a false positive, then time is wasted before re-insemination can occur because the false positive is unknown until the follow-up test.

Rather than yielding a false positive, the three-result pregnancy test may be calibrated to place the false positive into a recheck category, but while maintaining a high sensitivity. Samples of animals in the recheck category may indicate that the animal needs to be retested for pregnancy at a date after the first test. Testing at a later time may allow the pregnancy marker being detected to reach a testable level so that testing a later sample from the animal may yield the correct "not pregnant" or "pregnant" result. The recheck date may be earlier than the date of a standard follow-up procedure to confirm the results of the pregnancy test. Because the recheck can be performed onsite and visually using the systems and methods of the present disclosure, there may be time and cost savings associated with the recheck category for pregnancy management.

The three-result test may allow for more effective administration of hormones used to induce a new ovulation. Ovulation-inducing hormones are often administered after determining an animal is not pregnant. The hormones may allow the animal to return to heat and be mated again within a few days after the not pregnant determination. However, if a binary test yields a false negative for an animal that is otherwise pregnant, then the hormones administered to the animal may induce an abortion of a viable fetus. Allowing a classification of these false negatives as a recheck may allow follow-up testing within a week of the recheck result. As such, the false negative of a binary test and induced abortion may be avoided, saving time and money.

Another advantage of the recheck category may be physiological advantages associated with using a recheck category. For example, there are several physiological advantages to the recheck category when the pregnancy marker being detected is PSPB. One advantage is that, if an embryo dies, PSPB will stop being produced by the placenta but there will be residual PSPB in the blood. This is true no matter what form of PSPB molecule is being detected. The recheck category may be calibrated so that a residual level of PSPB in the blood indicates a retest. The PSPB will eventually clear from the blood and reach a non-detectable level. Taking a sample later for the recheck would likely indicate that the PSPB is below the cutoff and the animal is not pregnant following death of the embryo.

For example, if an animal loses an embryo anytime between about 30 days to about 75 days after insemination, it will take about 3 days to about 6 days for PSPB to clear from the blood. This is because the PSPB half-life in maternal serum is about 3 to 7 days, depending upon the variant of the PSPB molecule. If the high and low standards are properly calibrated to account for this, an initial check of a sample taken within this clearance time may indicate a recheck. For example, taking a sample 3 to 7 days after the initial sample was taken may be outside this clearance time and may indicate a not pregnant result.

Another physiological advantage is that the test will indicate a retest for some slowly developing embryos that are not producing enough PSPB at around 30 days-post insemination as to properly indicate whether the ruminant is pregnant. During the later retest, the result may indicate the ruminant is not pregnant if the embryo dies, or pregnant if the embryo grows.

Other advantages include that if a sample is withdrawn from a ruminant during the post-partum period when residual PSPB is present, then the test may indicate a recheck. If a sample is withdrawn from a ruminant during the post-partum period when residual PSPB is present, and new-embryo PSPB is present in low amounts, the test may also indicate a recheck. The later test can indicate correctly whether or not the ruminant is pregnant.

To achieve the above advantages for a three-result pregnancy test detecting PSPB, the high standard signal may be shifted lower to place fewer pregnant cows in the recheck category while still capturing a large percentage of the overlapping not pregnant cows as a recheck. As such, and just as an example, it may be possible to categorize during the initial check approximately 99% of the pregnant cows as pregnant and 90% of the not pregnant cows as not pregnant. The remaining cows may be categorized as a recheck. Those categorized as a recheck may be retested within a week with greater than 98% of the rechecked samples correctly being categorized as pregnant or not pregnant.

A three-result onsite, visual test may allow for achieving a higher specificity and sensitivity in a shorter testing period than possible with a two-result binary test.

Validation of Properly-Functioning Test

Methods may be employed to ensure that the test is properly calibrated and/or working. As an example, the high and low standards may be used as an initial check to determine if the test is properly calibrated and/or working. For example, the magnitude of the reaction (e.g., the signal or color intensity) for the high standard should be more intense than for the low standard. (The magnitude may be reversed in some embodiments such that the low standard may have a more intense signal or color than the high standard). If not, the test is not working properly. If the high and low standards look the same (e.g. signal or color intensity is same), then that may indicate the test is not working properly.

A test kit (such as Kits A-D in FIG. 2) may include a card with an indicia matching the magnitude of intensity (e.g., signal or color intensity) of the standards. If the intensity of the standards does not match the intensity on the color card, then the test may not be working properly.

The test kit may include (in addition to standards) containers of reagent solution with different sera of an animal that yield a test result of not pregnant and/or recheck and/or pregnant for the animal. These sera can be used to validate if the test yields the proper result for each sera and may therefore be functioning properly. One or a combination of the above can be used for validating if the test is working properly.

EXAMPLES

The following examples are included as non-exclusive, illustrative embodiments of the present disclosure. Those of skill in the art should, in light of the present disclosure, appreciate that many changes can be made in the specific embodiments which are disclosed and still obtain a like or similar result without departing from the spirit and scope of the present disclosure Example A Development of Reagents for ELISA Bovine PSPB (bPSPB) was isolated after the methods of Hamilton (1979), Butler (1980), and Butler et al., (1982) from placenta of cows that were less than 100 days in gestation; more specifically, they were from 25 to less than 100 days in gestation. The isolated PSPB was used to make standards. The high standard was made by diluting the PSPB to a concentration of 0.2 ng ml$^{-1}$ in steer serum or virgin heifer serum (VHS). The low standard was made by diluting the PSPB to a concentration of 0.1 ng ml$^{-1}$ in steer serum or VHS.

Additionally, PSPB was conjugated to tetanus toxoid and was used to immunize New Zealand White rabbits (Sasser et al., 1986). Anti-serum was collected and tested for reactivity to the bPSPB standards. A portion of the rabbit anti-serum was used for IgG isolation using a Protein G column (Pierce). The tetanus toxoid-conjugated PSPB was also used to immunize mice and develop monoclonal antibodies using procedures known to the art. These standards and antisera were used to develop various PSPB ELISA tests for pregnancy in livestock.

Ovine PSPB was isolated after the methods of Willard et al., 1995. Antisera against ovine PSPB was prepared as in Sasser et al., 1986. These reagents were used in the development of the ovine and caprine ELISA.

Buffers, chemicals and reagents were developed and used in a manner familiar to those skilled in the art of ELISA test development.

It will be appreciated that the development of the reagents, antibodies and standards for use with a cELISA for measuring estrone sulfate or progesterone can be developed in a manner familiar to those skilled in the art of ELISA test development.

Example B

Determination of Recheck Levels for PSPB

A test yielding pregnant, non-pregnant, and recheck cutoffs was developed based upon the radioimmunoassay (RIA) data of Sasser et al., 1986. Biol Reprod and Noyes et al., 1997. In the radioimmunoassay, a cutoff of 95 or 93% of buffer control of the binding of radio-iodinated PSPB was the inhibition required to reach a call of pregnancy for the test sample. Any lower percentages are all called pregnant. A percentage above 95 or 93% resulted in a non-pregnancy call. The nanogram amount of PSPB that gives a 93% radioimmunoassay cutoff was used as the cutoff in the ELISA plate test. It must be appreciated that protein isolates of PSPB protein fractions will have different specific activities (PSPB protein/total protein content of the preparation) between batches. The nanogram amount of high standard and low standard required in an assay to develop a cutoff must be tested against field samples from animals to learn the nanogram amount to use for the low and high standard. Knowing the pregnancy status of those animals at the preferred time of testing is necessary to assure that the nanogram amounts apply to the practice of blood-based pregnancy testing. Experience in use of the ELISA in cattle testing showed that a recheck range was needed in order to capture cattle that had PSPB in serum but at a level that warranted further testing to assure pregnancy or non-pregnancy.

These standard amounts provide guidelines for color development in a visual test for PSPB or other pregnancy markers. As an example for PSPB, a strong color indicates binding and substrate reactivity of the HRP-labeled antibody conjugate to the bound PSPB, and is a positive indication of pregnancy as would be the case, for example, in pregnant animals that are 30 days post breeding. Weak color development indicates little or no binding of the HRP-labeled antibody conjugate due to the absence of PSPB in the sample, and is a negative indication of pregnancy. Color development between standards indicates a recheck. Color for a recheck status could be indicative of embryonic death in previously pregnant cows; a value in late postpartum cows; a value in cows that were sampled too early in pregnancy; or a value, in rare cases, of cows with slow growing embryos. Standards of known concentrations of PSPB or other markers for pregnancy are run with each assay and are used to determine the visual color values for assigning pregnant, non-pregnant and recheck status.

Example C

ELISA for PSPB Detection Onsite with a Visual Result

The purified rabbit IgG from the Protein G column was labeled with biotin using an NHS-LC-Biotin labeling kit (Pierce). Following removal of excess biotin using a molecular weight cutoff spin column, the biotin labeled IgG (Biotin IgG) was diluted 1:2 in Stabilzyme stabilizer solution (SurModics, Inc) and further diluted to a final dilution of 1:2000 in Tris Buffered Saline with 1% bovine serum albumin and 0.05% TWEEN-20 polysorbate 20 (TBSTB) pH 7.4, and stored at 4 degrees Celsius.

Horseradish peroxidase—labeled Streptavidin (SA-HRP) was purchased from Pierce, diluted 1:100 in Stabilzyme stabilizer solution (SurModics, Inc) and further diluted to a final dilution of 1:5000 in TBSTB and stored at 4 degrees Celsius.

A NUNC C8 maxisorp strip well micro-titre clear or white polystyrene test plates were used for all tests (NUNC, Inc.). Maxisorp strip plates were coated with 150 microliters of anti-PSPB polyclonal rabbit anti-sera diluted 1:25000 in 0.1 M sodium carbonate buffer pH 9.6 for 18 hours at room temperature with constant agitation. Following coating, the solution was removed from the plates and 200 microliters of 0.5% bovine serum albumin in 0.1 sodium carbonate buffer pH 9.6 was added to each well and allowed to react for 15 minutes at room temperature with constant agitation. The plates were then washed four times with 300 microliters of Tris buffered saline with 0.05% TWEEN-20 polysorbate 20 (TBST), blotted dry on a paper towel, covered with parafilm and placed at 4 degree Celsius.

Before performing the assay on test samples, the coated strip plates, standards, Biotin IgG, SA-HRP, test samples, and buffers were allowed to equilibrate to room temperature. The appropriate number of strip wells were used to accommodate the number of test samples being tested, plus two wells for the high and low standards.

The strip wells were initially wetted with 40 microliters of sample buffer (80 mM sodium phosphate, 265 mM sodium chloride, 40 mM EDTA, 0.05% Proclin, 0.4% gelatin, 0.02% TWEEN-20 polysorbate 20, and a serum-based blocking agent (e.g., 5-15% of normal cow, deer, goat, mouse, rabbit, sheep, wild ruminant serum, etc.) using a drop bottle (one drop). A transfer pipette was then used to place 120 microliters (two drops) of the high standard in the upper left most well. Two drops of the low standard were placed in the well immediately below the high standard using a different transfer pipette. Each successive sample was added to the plate by transferring two drops with a new transfer pipette. The position of each sample was recorded on a grid consisting of 96 squares that represent the wells in a 96-well plate. The plate was gently swirled and allowed to incubate at room temperature on the bench top for 30 minutes. Following the incubation, the plate was emptied by pouring the samples out of the wells and lightly blotted on a paper towel. A squirt bottle was used to wash each well by filling the wells with TBST followed by removal of the solution and blotting on a paper towel. The washing was performed four times.

A dropper bottle was then used to add four drops (160 ul) of Biotin IgG (1:2000 in TBSTB) to each well. The plate was gently swirled and allowed to incubate at room temperature on the bench top for 15 minutes. Following the incubation, the plate was emptied by pouring the samples out of the wells and lightly blotted on a paper towel. A squirt bottle was used to wash each well by filling the wells with TBST followed by removal of the solution and blotting on a paper towel. The washing was performed four times.

A dropper bottle was then used to add four drops (160 ul) of SA-HRP (1:5000 in TBSTB from a 1 mg/ml stock solution) to each well. The plate was gently swirled and allowed to incubate at room temperature on the bench top for 15 minutes. Following the incubation, the plate was emptied by pouring the samples out of the wells and lightly blotted on a paper towel. A squirt bottle was used to wash each well by filling the wells with TBST followed by removal of the solution and blotting on a paper towel. The washing was performed four times.

Four drops of TMB Max (Neogen Inc.) were added to each well using a dropper bottle. The enzymatic reaction between the HRP and TMB was allowed to proceed for five minutes. During this time, a blue color became apparent in the standard wells and samples that contained PSPB. At five minutes, a dropper bottle was used to add 1 drop (40 microliters) of 2% sodium fluoride to each well.

Each well was then compared visually with the high and low standard wells. Samples that achieved a signal that was equal to or greater than the high standard were categorized as pregnant. Samples with a signal less than the low standard were categorized as not pregnant. Samples that had signals that fall between the two standards were categorized as recheck.

It is to be appreciated that ovine, caprine, cervid and other domestic and wild ruminant animals can be tested for pregnancy by this method of visual detection of the test sample.

Pregnancy status categorization of cows using these standards was confirmed using a commercially available laboratory assay of BioTracking LLC. In the confirmation assay, the optical density for each well was obtained from a plate reader with a 650 nanometer filter before stopping the enzymatic reaction (VersaMax, Molecular Devices, Inc). The enzymatic reactions were stopped with 1M sulfuric acid and read using a plate reader with a 450 nanometer filter (VersaMax, Molecular Devices, Inc).

Example D

Use of Various Visual Classification in Animal Management

As embryos and placenta grows, there is an increase in development of binucleated cells within the trophoblastic ectoderm of the conceptus. These cells are the source of PSPB in the maternal blood (Eckblad et al., 1985). As time progresses from conception to 30 days in gestation, the concentration of PSPB in blood increases from non-detectable levels to fully detectable levels. Some cows have PSPB in serum beginning at 15 days after breeding while all have it by 28 (Sasser et al., 1986) to 30 (Humblot et al. 1988) days. The BioPRYN test is used to detect pregnancy from 30 days until term pregnancy (Howard et al, 2007). Likewise, if an embryo dies after there is a detectable level of PSPB in serum of the mother then PSPB will decline to non-detectable levels. The half-life of PSPB in serum is approximately 7 days in postpartum cows (Kirakofe et al., 1993) or cows in which embryonic death was induced by infection of the uterus (Semambo et al., 1992).

During either the incline of embryo growth or decline after embryo death or parturition, there is a period of time in which marginal levels of PSPB are present in serum. This results in uncertainty in prediction of pregnancy status leading to placing cows in the recheck category. An ELISA assay that detects PSPB in bovine sera binds PSPB to antibodies (anti-PSPB) coated in the wells and PSPB is detected by secondary binding of horseradish peroxidase (HRP)-labeled anti-PSPB antibodies. Binding of the HRP-labeled antibody conjugate is detected by the addition of 3,3',5,5'-tetramethylbenzidine (TMB) and is quantified by the subsequent color development. A strong color indicates binding and substrate reactivity of the HRP-labeled antibody conjugate to the bound PSPB, and is a positive indication of pregnancy as would be the case, for example, in pregnant animals that are 30 days post breeding. Weak color development indicates little or no binding of the HRP-labeled antibody conjugate due to the absence of PSPB in the sample, and is a negative indication of pregnancy. Color development between standards indicates a recheck. Color for a recheck status could be indicative of embryonic death in previously pregnant cows; a value in late postpartum cows; a value in cows that were sampled too early in pregnancy; or a value, in rare cases, of cows with slow growing embryos. Standards of known concentrations of PSPB are run with each assay and are used to determine the visual color values for assigning pregnant/not pregnant and recheck status.

Over time, the level of PSPB in sera of cows with early growing embryos will change over time. The levels of PSPB in sera of cows during the postpartum period; cows will transition from a high degree of color for a positive postpartum cow to a moderate color for a recheck postpartum cow to a low or no color for non-pregnant postpartum cow or cows with embryonic death. Cows are known to transition to the non-pregnant status between 50 and 90 days postpartum (Kirakofe et al. 1993).

The economic value of a visual recheck category exists. For example, if a cow is 30 days in gestation and the test reveals a recheck, the cow can be tested within 3 to 7 days to confirm the status because the PSPB value will either increase into the pregnancy status or decline into the non pregnancy status. Within this time period, 87 percent of the recheck cows will likely be not pregnant on the next test while 13 percent will be pregnant (Biotracking LLC, unpublished). Under the conventional rectal palpation method, these cows would be tested again at 60 to 80 days after breeding and time in being non-pregnant is extended. There is therefore considerable cost and time savings to the farming operation by using an onsite test employing the visual recheck. Likewise, rectal palpation is not done until 35 or later after breeding. Finding the non-pregnant cows earlier with PSPB analysis using an onsite test employing the visual recheck saves time and money in learning of the non-pregnant cows. These cows can be treated with hormones to initiate heat and re-breed immediately. Thus the recheck category coupled with early testing is extremely valuable to management of the animals.

Additionally, using the recheck status by visual color development in a test allows for more clearly identifying the non-pregnant cow at an earlier time. Placing cows into the Recheck category allowed for safe identification of pregnant cows as early as 28 days after AI. Seven percent of pregnant cows were placed in the non-pregnant category on Day 26. By Day 28 none of the pregnant cows were so placed while on this day some were in the Recheck category. Thus management can safely treat those categorized as non-pregnant without aborting any embryos. They can also retest the recheck cows within a week after the previous testing to specifically categorize the pregnancy status. This retest saves time in re-breeding non-pregnant cows. Additionally, it is possible to place more animals in the recheck rather than non-pregnant category by lowering the visible cutoff for the recheck range. This would allow earlier testing and capture, as recheck, more animals classified as non-pregnant such that they will be tested again within a week to better identify the status. Many of these will end up in the pregnant category because they were low in PSPB because of early testing, not embryonic death. This modification of the recheck category allows to test earlier and identify non-pregnant cow for early re-breeding.

Optical density is an indicator of visual color and a measure of PSPB in serum of cows, sampled twice daily, that were pregnant or not pregnant. The Repeat Range is an OD value that indicates that the cow must be tested again to get a definitive result. Within one to two days, the OD progressed from low color to a color indicative of pregnancy. If an embryo has died at 28 days after AI, the OD would decline again through the Repeat Range and then to the non-pregnant range. In groups of cows, there will be those in the Repeat category due to delayed embryo growth or early testing or embryo death.

Example E

Ovine (Sheep)/Caprine (Goat) Pregnancy ELISA Assay for the Laboratory

This antigen-capture, or "sandwich," ELISA detects PSPB in ovine or caprine sera. Serum PSPB binds to antibodies coated in the wells and is detected by secondary binding of a labeled antibody. Binding of the labeled antibody conjugate is detected by the addition of the enhancer (e.g. SA-HRP) and 3,3',5,5'-tetramethylbenzidine (TMB) and is quantified by the subsequent color development. A strong color indicates binding and substrate reactivity of the labeled antibody conjugate to the bound PSPB, and is a positive indication of pregnancy. Weak color development indicates little or no binding of the labeled antibody conjugate due to the absence of PSPB in the sample, and is a negative indication of pregnancy. Color development between the standards indicates a recheck. Standards of known concentrations of PSPB are run with each assay and are used to determine the optical density values for assigning Pregnant/Not Pregnant ranges.

| | Components of the Assay | Levels |
|---|---|---|
| A | Antibody coated plates | 5 |
| B | SG Sample Buffer | 30 ml |
| C | Open Goat Serum (OGS) | None |
| D | PSPB Standard: High Standard | 9 ml |
| E | PSPB Standard: Low Standard | 9 ml |
| F | Pregnant Goat Serum (PGS) | None |
| G | SG Conjugate Buffer | 250 ml |
| H | B6 rabbit α-bovine PSPB conjugate | 750 µl |
| I | Enhancer (e.g., SA-HRP) | 400 µl |
| J | 20X Wash Buffer concentrate | 120 ml |
| K | 250X TMB Substrate Solution | 1.5 ml |
| L | Phosphate-Citrate Buffer | 125 ml |

Other Materials for Performing Test

Single and multichannel adjustable volume pipettors and disposable tips. Multichannel pipettor reservoirs. Microplate reader with the capability to read at 650 (or 630) and 450 nm. Deionized or distilled water. Graduated cylinders and beakers. Manual or automatic plate washer. Timer. Platform shaker and shaker/incubator. Microtiter plate covers. 3% hydrogen peroxide. Stop solution (1M $H_2SO4$).

Storage and Stability

Store all reagents except for the 20× wash buffer (J) at 4° C. The wash buffer concentrate must be stored at room temperature. Reagents will remain stable when stored as indicated.

Assay Procedure

1. Warm up all kit reagents, plates and samples.
2. Prepare the plates (A). Add 50 µl of SG Sample Buffer (B) (SG Sample buffer can be 80 mM sodium phosphate, 265 mM sodium chloride, 80 mM EDTA, 0.05% Proclin, 0.4% gelatin, 0.02% TWEEN-20 polysorbate 20, and a serum-based blocking agent (e.g., 5-15% of normal cow, deer, goat, mice, rabbit, sheet, wild ruminant serum, etc.) to each well.
3. Add controls and samples. Run 150 µl of the controls provided with the kit as follows. Use a fresh tip for each solution:

| | |
|---|---|
| Well A-1: | OGS (Open Goat Serum) (C) |
| Wells B, C, D-1 | PSPB Standard: High Standard (D) |
| Wells E, F, G-1 | PSPB Standard: Low Standard (E) |
| Well H-1: | PGS (Pregnant Goat Serum) (F) |

Add 150 µl of serum to the remaining wells. Use a fresh tip for each sample.

4. Incubate the plates. Seal the wells with ParaFilm or DuraSeal, cover with a microplate lid, and incubate overnight at room temperature with shaking.

5. Prepare the Conjugate. Prepare 1× antibody conjugate by diluting 2 parts of the B6 conjugate (H) with 998 parts of SG Conjugate Buffer (G) (SG Conjugate Buffer can be 40 mM sodium phosphate, 132.5 mM sodium chloride, 20 mM EDTA, 0.05% Proclin, 0.2% gelatin, 0.01% TWEEN-20 polysorbate 20, and a serum-based blocking agent (e.g., 5-15% of normal cow, deer, goat, mice, rabbit, sheet, wild ruminant serum, etc.). For 96 wells, mix 40 μl of the B6 conjugate (H) with 20 ml of SG Conjugate Buffer (G).

6. Prepare the Wash Solution. Prepare 1× Wash Buffer by diluting one part of the 20× Wash Buffer Concentrate (J) (20× Wash Buffer Concentrate can be 200 mM sodium phosphate, 2.4 M sodium chloride, 0.5% TWEEN-20 polysorbate 20) with 19 parts of deionized or distilled water. Approximately 3 ml/well of 1× wash solution will be required for this wash step and the wash step below for a total of 9 washes.

7. Wash wells 4 times: After the overnight incubation, remove the ParaFilm or DuraShield and wash the plate four times. Save the DuraShield for the next incubation.

If an automatic washer is used, place the plate on the washer and wash 4 times with a volume of 300 μl. Set the washer to soak for 10 seconds and aspirate for 4 seconds between each wash. Remove any residual wash solution by striking the inverted plate on a paper towel (blot dry). If manual washing is used, dump the contents of the wells into a sink or tub and then blot dry. Using a multichannel pipettor or Repeat Pipettor, add 300 μl of 1× wash buffer to each well and swirl the plate for 10 seconds. Repeat the washing procedure 3 more times (4 washes total).

8. Add Conjugate: Using a single- or multi-channel pipettor, add 200 μl of the conjugate from step 5 to each well. Cover with fresh ParaFilm or the DuraSeal from Step 4, and incubate at 37° C. and 100 RPM for 60 minutes.

9. Prepare Enhancer. Prepare 1× Enhancer by diluting 1.25 parts of the Enhancer (I) with 998.75 parts of SG Conjugate Buffer (G). For 96 wells, mix 25 μl of the Enhancer (I) with 20 ml of QUICK Buffer (G) (Quick Buffer can be phosphate buffered saline pH 7.2 with 0.5% bovine serum albumin and 0.05% TWEEN-20 polysorbate 20).

10. Dump, blot and wash the wells 1 time. After the 60 minute incubation listed in Step 8, dump out the conjugate solution and blot dry on a paper towel. Wash the plate one time with 1× wash buffer. Dump out the wash solution and blot dry on a paper towel.

11. Add Enhancer. Using a single- or multi-channel pipettor, add 200 μl of the conjugate from step 9 to each well. Cover with fresh ParaFilm or the DuraSeal from Step 4, and incubate at 37° C. with shaking for 60 minutes.

12. Wash wells 4 times: After the 60 minute incubation listed in Step 11, repeat the washing procedure described in Step 7, using the remaining 1× wash buffer (4 washes total).

13. Prepare the substrate solution: Prepare 1×TMB substrate by diluting one part of the 250×TMB Substrate solution (K) with 250 parts of Phosphate-Citrate Buffer (L) (Phosphate citrate buffer can be 50 mM sodium phosphate adjusted to pH 4.5 with citric acid). It is not necessary to adjust for the slight volume change. For 96 wells (20 ml total volume), add 80 μl of TMB Substrate Solution (K) to 20 ml of Phosphate-Citrate Buffer (L) and mix well by swirling in a beaker. Add 40 μl of 3% hydrogen peroxide and mix well.

14. Add substrate solution: Add 200 μl of the substrate solution prepared in Step 13 to each well. After all of the wells have been filled, gently mix by swirling a few times in each direction. Incubate at room temperature for 15 minutes, swirl the plate for 5 seconds, and immediately read the plate at 650 or 630 nm. If the average OD of the high standards is not approximately 0.12, continue the incubation for 2 additional minutes and repeat the reading. When the average OD of the high standards is between 0.12 and 0.15, add the stop solution.

15. Add the Stop Solution: Add 100 μl of the stop solution (1M $H_2SO_4$) to each well. After all of the wells have been filled, gently mix the well contents by swirling a few times in each direction. Add the stop solution in the same order and timing as was done for the TMB.

16. Read the plate: Within 30 minutes after adding the stop solution, the plate should be read on a plate reader at 450 nm. For Molecular Devices scanners running SOFTmax software, export the reading as a text file for data analysis.

NOTE: This test is time dependent and assumes loading of a plate takes less than 30 minutes at room temperature. If the sample loading procedure takes longer than this prescribed time, or if loading multiple plates, pre-plate and transfer samples and standards with a multi-channel pipettor using a new tip for each sample.

Example F

Quick Test: Bovine Pregnancy ELISA Assay

This antigen-capture, or "sandwich," ELISA detects PSPB in bovine sera. Serum PSPB binds to antibodies coated in the wells and is detected by secondary binding of a labeled antibody. Binding of the labeled antibody conjugate is detected by the addition of the enhancer (e.g. SA-HRP) and 3,3',5,5'-tetramethylbenzidine (TMB) and is quantified by the subsequent color development. A strong color indicates binding and substrate reactivity of the labeled antibody conjugate to the bound PSPB, and is a positive indication of pregnancy. Weak color development indicates little or no binding of the labeled antibody conjugate due to the absence of PSPB in the sample, and is a negative indication of pregnancy. Color development between the standards indicates a recheck. Standards of known concentrations of PSPB are run with each assay and are used to determine the optical density values for assigning Pregnant/Not Pregnant ranges.

| | Components of the Assay | Amount |
|---|---|---|
| A | Antibody coated plates | 3 |
| B | Sample Buffer | 1 bottle |
| C | Virgin Heifer Serum (VHS) | 2 vials |
| D | PSPB Standard: QUICK Hi Std | 1 vial |
| E | PSPB Standard: QUICK Lo Std | 1 vial |
| F | Pregnant Cow Serum (PCS) | 2 vials |
| G | QUICK Buffer | 1 bottle |
| H | Detector concentrate | 1 vial |
| I | Enhancer concentrate (SA-HRP) | 1 vial |
| J | 20X Wash Buffer concentrate | 1 bottle |
| K | TMB Substrate concentrate | 1 vial |
| L | QUICK Phosphate-Citrate Buffer | 1 bottle |

Other Materials Needed for Test

Single and multichannel adjustable volume pipettors and disposable tips. Multichannel pipettor reservoirs. Microplate reader with the capability to read at 650 (or 630) and 450 nm. Deionized or distilled water. Graduated cylinders and beakers. Manual or automatic plate washer. Timer. Microtiter plate covers. 3% hydrogen peroxide. Stop solution (1M $H_2SO_4$).

Storage and Stability

Store all reagents except for the 20× wash buffer (J) at 4° C. The wash buffer concentrate must be stored at room temperature. Reagents will remain stable when stored as indicated.

Assay Procedure

Pre-plate by aliquoting serum samples to an empty microtiter plate when assaying large numbers of samples 1. Warm up all kit reagents, plates and samples.
2. Prepare the plates (A). Add 50 μl of Sample Buffer (B) to each well.
3. Add controls and samples. Run 150 μl of the controls provided with the kit as follows. Use a fresh tip for each solution:

| | |
|---|---|
| Well A-1: | VHS (Virgin Heifer Serum) (C) |
| Wells B, C, D-1 | PSPB Standard: High Standard (D) |
| Wells E, F, G-1 | PSPB Standard: Low Standard (E) |
| Well H-1: | PCS (Pregnant Cow Serum) (F) |

Add 150 μl of serum to the remaining wells. Use a fresh tip for each sample.

4. Incubate the plates. Seal the wells with ParaFilm or DuraSeal, cover with a microplate lid, and incubate for one hour at room temperature (at or near 70 degrees Fahrenheit).
5. Prepare the Detector Solution. Prepare 1× Detector solution by diluting 6 parts of the Detector concentrate (H) with 994 parts of QUICK Buffer (G) (Quick Buffer can be phosphate buffered saline pH 7.2 with 0.5% bovine serum albumin and 0.05% TWEEN-20 polysorbate 20). For 96 wells, mix 120 μl of the Detector (H) with 20 ml of QUICK Buffer (G).
6. Prepare the Wash Solution. Prepare 1× Wash Buffer by diluting one part of the 20× Wash Buffer Concentrate (J) with 19 parts of deionized or distilled water. Approximately 3 ml/well of 1× wash solution will be required for this wash step and the wash step below for a total of 9 total washes.
7. Wash wells 4 times: After the one hour incubation, remove the ParaFilm or DuraShield and wash the plate four times. Save the DuraShield for the next incubation. If using more than one plate dump all plates at the same time to keep timing consistent.

If an automatic washer is used, place the plate on the washer and wash 4 times with a volume of 300 μl. Set the washer to soak for 10 seconds and aspirate for 4 seconds between each wash. Remove any residual wash solution by striking the inverted plate on a paper towel (blot dry). If manual washing is used, dump the contents of the wells into a sink or tub and then blot dry. Using a multichannel pipettor or RepeatPipettor, add 300 μl of 1× wash buffer to each well and swirl the plate for 10 seconds. Repeat the washing procedure 3 more times (4 washes total).

8. Add Detector Solution: Using a single- or multi-channel pipettor, add 200 μl of the conjugate from Step 5 to each well. Cover with fresh ParaFilm or the DuraSeal from Step 4, and incubate at room temperature for one hour.
9. Prepare Enhancer solution. Prepare 1× Enhancer solution by diluting 2 parts of the Enhancer concentrate (I) with 998 parts of QUICK Buffer (G). For 96 wells, mix 40 μl of the Enhancer (I) with 20 ml of QUICK Buffer (G).
10. Dump, blot and wash the wells 1 time. After the one hour incubation listed in Step 8, dump out the conjugate solution and blot dry on a paper towel. Wash the plate one time with 1× wash buffer. Dump out the wash solution and blot dry on a paper towel.
11. Add Enhancer solution. Using a single- or multi-channel pipettor, add 200 μl of the conjugate from step 9 to each well. Cover with fresh ParaFilm or the DuraSeal from Step 4, and incubate at room temperature one hour.
12. Wash wells 4 times: After the one hour incubation listed in Step 11, repeat the washing procedure described in Step 7, using the remaining 1× wash buffer (4 washes total).
13. Prepare the substrate solution: Prepare TMB substrate by diluting three parts of the TMB Substrate solution (K) with 250 parts of QUICK Phosphate-Citrate Buffer (L). It is not necessary to adjust for the slight volume change. For 96 wells (20 ml total volume), add 240 μl of TMB Substrate Solution (K) to 20 ml of QUICK Phosphate-Citrate Buffer (L) and mix well by swirling in a beaker. Add 40 μl of 3% hydrogen peroxide and mix well.
14. Add TMB substrate solution: Add 200 μl of the TMB substrate solution prepared in Step 13 to each well. After all of the wells have been filled; gently mix by swirling a few times in each direction. Incubate at room temperature for 10 minutes, swirl the plate for 5 seconds, and immediately read the plate at 650 or 630 nm. If the average OD of the high standards is not approximately 0.35, continue the incubation for 2 additional minutes and repeat the reading. When the average OD of the high standards is between 0.35 and 0.4, add the stop solution.
15. Add the Stop Solution: Add 100 μl of the stop solution (1M $H_2SO_4$) to each well. After all of the wells have been filled; gently mix the well contents by swirling a few times in each direction. Add the stop solution in the same order and timing as was done for the TMB.
16. Read the plate: Within 30 minutes after adding the stop solution, the plate should be read on a plate reader at 450 nm. For Molecular Devices scanners running SOFTmax software, export the reading as a text file for data analysis.

NOTE: This test is time dependent and assumes loading of a plate takes less than 30 minutes at room temperature. If the sample loading procedure takes longer than this prescribed time, or if loading multiple plates, pre-plate and transfer samples and standards with a multi-channel pippetor using a new tip for each sample.

Example G

Rapid ELISA for PSPB Detection

This antigen-capture, or "sandwich," ELISA detects PSPB in bovine sera. Serum PSPB binds to antibodies coated in the wells and is detected by secondary binding of a labeled antibody. Binding of the labeled antibody conjugate is detected by the addition of the Enhancer and 3,3',5,5'-tetramethylbenzidine (TMB) and is quantified by the subsequent color development. A strong color indicates binding and substrate reactivity of the labeled antibody conjugate to the bound PSPB, and is a positive indication of pregnancy. Weak color development indicates little or no binding of the labeled antibody conjugate due to the absence of PSPB in the sample, and is a negative indication of pregnancy. Color development between the standards indicates a recheck. Standards of known concentrations of PSPB are run with each assay and are used to determine the optical density values for assigning pregnant/not pregnant ranges.

| | Components of the Assay | Amounts |
|---|---|---|
| A | Antibody coated plates | 5 |
| B | Sample Buffer | 30 ml |
| C | Virgin Heifer Serum (VHS) | 4 ml |

| Components of the Assay | Amounts |
| --- | --- |
| D    PSPB High Standard | 9 ml |
| E    PSPB Low Standard | 9 ml |
| F    Pregnant Cow Serum (PCS) | 4 ml |
| G    QUICK Buffer | 125 ml |
| H    B6 rabbit α-bovine PSPB conjugate | 750 µl |
| I    Enhancer (SA-HRP) | 400 µl |
| J    20X Wash Buffer concentrate | 120 ml |
| K    250X TMB Substrate Solution | 1.5 ml |
| L    QUICK Phosphate-Citrate Buffer | 125 ml |

Other Materials

Single and multichannel adjustable volume pipettors and disposable tips. Multichannel pipettor reservoirs. Microplate reader with the capability to read at 650 (or 630) and 450 nm. Deionized or distilled water. Graduated cylinders and beakers. Manual or automatic plate washer. Timer. Platform shaker and shaker/incubator. Microtiter plate covers. 3% hydrogen peroxide. Stop solution (1M $H_2SO_4$).

Storage and Stability

Store all reagents except for the 20× wash buffer (J) at 4° C. The wash buffer concentrate must be stored at room temperature. Reagents will remain stable when stored as indicated.

Assay Procedure

1. Warm up all kit reagents, plates and samples.
2. Prepare the plates (A). Add 50 µl of Sample Buffer (B) to each well.
3. Add controls and samples. Run 150 µl of the controls provided with the kit as follows. Use a fresh tip for each solution:

| | |
| --- | --- |
| Well A-1: | VHS (Virgin Heifer Serum) (C) |
| Wells B, C, D-1 | PSPB Standard (D) |
| Wells E, F, G-1 | PSPB Standard (E) |
| Well H-1: | PCS (Pregnant Cow Serum) (F) |

Add 150 µl of serum to the remaining wells. Use a fresh tip for each sample.
4. Incubate the plates. Seal the wells with ParaFilm or DuraSeal, cover with a microplate lid, and incubate for one hour at 37° C. with shaking.
5. Prepare the Conjugate. Prepare 1× antibody conjugate by diluting 6 parts of the B6 conjugate (H) with 994 parts of QUICK Buffer (G) (Quick Buffer can be phosphate buffered saline pH 7.2 with 0.5% bovine serum albumin and 0.05% TWEEN-20 polysorbate 20). For 96 wells, mix 120 µl of the B6 conjugate (H) with 20 ml of QUICK Buffer (G).
6. Prepare the Wash Solution. Prepare 1× Wash Buffer by diluting one part of the 20× Wash Buffer Concentrate (J) with 19 parts of deionized or distilled water. Approximately 3 ml/well of 1× wash solution will be required for this wash step and the wash step below for a total of 9 washes.
7. Wash wells 4 times: After the overnight incubation, remove the ParaFilm or DuraShield and wash the plate four times. Save the DuraShield for the next incubation.
   a. If an automatic washer is used, place the plate on the washer and wash 4 times with a volume of 300 µl. Set the washer to soak for 10 seconds and aspirate for 4 seconds between each wash. Remove any residual wash solution by striking the inverted plate on a paper towel (blot dry).
   b. If manual washing is used, dump the contents of the wells into a sink or tub and then blot dry. Using a multichannel pipettor or RepeatPipettor, add 300 µl of 1× wash buffer to each well and swirl the plate for 10 seconds. Repeat the washing procedure 3 more time (4 washes total).
8. Add Conjugate: Using a single- or multi-channel pipettor, add 200 µl of the conjugate from step 5 to each well. Cover with fresh ParaFilm or the DuraSeal from Step 4, and incubate at 37° C. and 100 RPM for 30 minutes.
9. Prepare Enhancer. Prepare 1× Enhancer (SA-HRP) by diluting 2.5 parts of the Enhancer (I) with 997.5 parts of QUICK Buffer (G). For 96 wells, mix 50 µl of the Enhancer (I) with 20 ml of QUICK Buffer (G).
10. Dump, blot and wash wells 1 time. After the 30 minute incubation listed in Step 8, dump out conjugate solution and blot dry on a paper towel. Wash plate one time with 1× wash buffer. Dump out the wash solution and blot dry on a paper towel.
11. Add Enhancer. Using a single- or multi-channel pipettor, add 200 µl of the conjugate from step 9 to each well. Cover with fresh ParaFilm or the DuraSeal from Step 4, and incubate at 37° C. with shaking for 30 minutes.
12. Wash wells 4 times: After the 30 minute incubation listed in Step 11, repeat the washing procedure described in Step 7, using the remaining 1× wash buffer (4 washes total).
13. Prepare the substrate solution: Prepare 3×TMB substrate by diluting three parts of the 250×TMB Substrate solution (K) with 250 parts of QUICK Phosphate-Citrate Buffer (L). It is not necessary to adjust for the slight volume change. For 96 wells (20 ml total volume), add 240 µl of TMB Substrate Solution (K) to 20 ml of QUICK Phosphate-Citrate Buffer (L) and mix well by swirling in a beaker. Add 40 µl of 3% hydrogen peroxide and mix well.
14. Add substrate solution: Add 200 µl of the substrate solution prepared in Step 13 to each well. After all of the wells have been filled, gently mix by swirling a few times in each direction. Incubate at room temperature for 15 minutes, swirl the plate for 5 seconds, and immediately read the plate at 650 or 630 nm. If the average OD of the high standards is not approximately 0.18, continue the incubation for 2 additional minutes and repeat the reading. When the average OD of the high standards is between 0.18 and 0.19, add the stop solution.
15. Add the Stop Solution: Add 100 µl of the stop solution (1M $H_2SO_4$) to each well. After all of the wells have been filled, gently mix the well contents by swirling a few times in each direction. Add the stop solution in the same order and timing as was done for the TMB.
16. Read the plate: Within 30 minutes after adding the stop solution, the plate should be read on a plate reader at 450 nm. For Molecular Devices scanners running SOFTmax software, export the reading as a text file for data analysis.

Note: This test is time dependent and assumes loading of a plate takes less than 30 minutes at room temperature. If the sample loading procedure takes longer than this prescribed time, or if loading multiple plates, please pre-plate and transfer samples and standards with a multi-channel pippetor using a new tip for each sample.

Example H

Competitive ELISA (cELISA) Protocol Using Progesterone for Pregnancy Detection

1. Use the NUNC maxisorp plate that has been coated with antibody to rabbit anti-progesterone antibody and blocked with bovine serum albumin.

2. There are Control vials consisting of one vial contains high progesterone, one vial containing no progesterone.
3. There are five Standard vials containing 100, 25, 6.25, 1.56, and 0.39 ng/mL progesterone diluted in bull serum.
4. Prepare conjugate. There is one vial that contains progesterone-HRP conjugate (at a dilution of 1:100). Prepare a 1:200,000 dilution using the enzyme-linked immunoassay (EIA) buffer (Phosphate buffered saline, 0.1 M, pH 7.0). For one full plate, add 4.25 μl progesterone-HRP (1:100) to 8.495 mL conjugate buffer. Use correct lesser proportions if less than a full plate is needed.
5. Add 30 μl/well of bull serum, each of the five standards of progesterone, two controls to appropriate wells of the plate.
6. Add 30 μl/well per well of unknown serum from test animals to appropriate wells.
7. Add 70 μl per well of conjugate (prepared as above) using a multi-channel pipette. Incubate at room temperature for two hours.
8. Wash the plate 4 times with 300 μl per well each time using wash buffer (phosphate buffered saline, pH 7.2, 0.02% TWEEN-20 polysorbate 20). Use a multichannel pipette or a plate washer. Wash buffer is provided as a 10× concentrate. For a full plate, prepare a dilution of 120 mL by adding 12 mL of 10× to 108 mL of distilled water.
9. Prepare 10 mL per full plate of the TMB substrate dilution. Use the phosphate/citrate buffer (0.05 M Citric Acid, pH 4.0) that is provided in proportion to the amount of wells that were used in the plate. Make the dilution by adding 40 μl (4 μl/mL) of sTMB and 20 μl (2 μl/mL) of hydrogen peroxide (not provided; a 3% solution to be purchased from a drug store) solution to 10 mL of phosphate/citrate buffer. Use 100 μL per well.
10. Incubate for 15 to 20 minutes based upon the color development.
11. Add 100 μl/well 1M $H_2SO4$ to stop the reaction and read at 450 nm.
12. Calculate the results by using the standard curve after methods known to those skilled in the art to calculate quantity (ng/mL) of progesterone in test samples. Apply results known to those skilled in the art acknowledging the time for sampling the animal after insemination and quantity of progesterone that is expected in not pregnant or pregnant animals at time of next expected heat.

Example I

Competitive ELISA (cELISA) Protocol for Estrone Sulfate for Mares

Protocol
1. Use the NUNC maxisorp plate that has been coated with antibody to estrone conjugate and blocked with bovine serum albumin.
2. There are Control vials consisting of one vial contains gelding serum, one vial containing pregnant mare serum and one vial containing non-pregnant mare serum.
3. There are five Standard vials containing 81, 27, 9, 3, and 1 ng/mL estrone sulfate diluted in gelding serum.
4. Prepare conjugate. There is one vial that contains estrone sulfate-HRP conjugate (at a dilution of 1:100). Prepare a 1:350,000 dilution using the enzyme-linked immunoassay (EIA) buffer (Phosphate buffered saline, 0.1 M, pH 7.0). For one full plate, add 2.43 μl estrone sulfate-HRP (1:100) to 8.498 mL conjugate buffer. Use correct lesser proportions if less than a full plate is needed.
5. Add 20 μl/well of gelding serum, each of the five standards of estrone sulfate, pregnant mare serum and open mare serum to appropriate wells of the plate (see plate grid protocol).
6. Add 20 μl/well per well of unknown serum from test animals to appropriate wells.
7. Add 80 μl per well of conjugate using a multi-channel pipette. Incubate at room temperature for two hours.
8. Wash the plate 4 times with 300 ul per well each time using wash buffer (phosphate buffered saline, pH 7.2, 0.02% TWEEN-20 polysorbate 20). Use a multichannel pipette or a plate washer. Wash buffer is provided as a 10× concentrate. For a full plate, prepare a dilution of 120 mL by adding 12 mL of 10× to 108 mL of distilled water.
9. Prepare 10 mL per full plate of the TMB substrate dilution. Use the phosphate/citrate buffer (0.05 M Citric Acid, pH 4.0) that is provided in proportion to the amount of wells that were used in the plate. Make the dilution by adding 40 μl (4 μl/mL) of sTMB and 20 μl (2 μl/mL) of hydrogen peroxide (not provided; a 3% solution to be purchased from a drug store) solution to 10 mL of phosphate/citrate buffer. Use 100 μl per well.
10. Incubate for 10 to 15 minutes based upon the color development.
11. Add 100 μl/well 1M $H_2SO4$ to stop the reaction and read at 450 nm.
12. Read the plate at 450 nm on a plate reader. Use the standard curve, after methods known to those skilled in the art to calculate the quantity (ng/mL) of estrone sulfate in test samples.
13. Use the following cutoffs for indication of pregnancy status:

| | |
|---|---|
| 1. Not pregnant mares or pregnant less than 35 days: | 0-5 ng/mL |
| 2. Not pregnant or pregnant between 0 and 70 days: | >5-13 ng/mL |
| 3. Pregnant, questionable value: | 9.5-13 ng/mL |
| 4. Mares that are 70 or more days in pregnancy: | >13 ng/mL |

Example J

Stabilized Plate Protocol

The stabilizer may improve the shelf-life of the plates that are used in the assay. Following the below procedure, a plate may maintain immunological activity for several months rather than 1 to 3 months (with declining immunoactivity) when not stabilized.

For 1 liter of stabilized block solution (25 ml per 96-well plate if using 250 uL per well) use the following phosphate buffer containing salt, sugar and a protein.

0.21 g $NaH_2PO4$
1.17 g $Na_2HPO4$
7 g NaCl
pH 7.4

Add 50 grams of sucrose and 5 grams of bovine serum albumin (BSA) per liter.

First, the wells of plates are coated with a BRE (e.g., proteins such as antibodies against PSPB or an antigen such as PSPB). This is done by overnight incubation with the BRE (varied concentrations) in 200 microliters (or varied volumes) of bicarbonate buffer, pH 9.4 to 9.6. The plates are then washed four times (or varied times) with wash buffer and are blotted dry. Then 250 ul (or varied volumes but always more than the volume of the coating buffer) of stabilized blocker is added to the wells of the plate. Leave the plate on an orbital shaker for one hour. Empty the stabilized blocking solution by inversion and shaking and blot dry. Place the plate in an incubator at 37 degrees centigrade for 2 hours for drying. Cover the plate with ParaFilm or a plate sealer as desired. Alternatively, place un-covered plates into airtight bags (i.e. Mylar foil) that contains a desiccant packet and store at about 4 degrees C.

Possible Permutations for a Stabilizer:

Blocking materials: Various proteins (BSA, casein) and/or surfactant TWEEN-20 polysorbate 20, TWEEN-80 polysorbate 80, polyethylene glycol, Triton x-100)

Sugars: Use in combination with non-reducing sugar at 0.25% to 20% (weight/volume). Example of sugars that are non-reducing sugars such as sucrose, trehalsoe, etc., Buffers: Use of different buffers such as phosphate (as above), carbonate, TRIS, MOPSO, MES.

As for the effectiveness of the stabilizer, after 14 weeks at room temperature, a plate containing only dry BSA (a routine method of blocking) as a blocker had a 50% decrease in ELISA OD signal and a 100% increase in background compared to newly manufactured plates with the dry BSA blocker. The plates stored at room temperature for 14 weeks with the above "stabilized blocker" had the same signal and background as newly prepared plates.

Following the above procedure may allow a test surface coated with the stabilizer to be stored at room temperature (about 20° C. (68° F.) to about 25° C. (77° F.) for about 14 weeks with the test surface having the same signal and background as newly prepared test surfaces where the signal and background were measured within 1 day after being coated.

REFERENCES

All of the following references are specifically incorporated herein by reference:

Batistaa A, Beckers J F, Caleroa P, Graciaa A, Gonzalez F, Sulon J. 2001. Pregnancy-associated glycoproteins (PAG) detection in milk samples for pregnancy diagnosis in dairy goats. Theriogenology 56:671-676.

Prakash B, Telugu V L, Walker A M, and Green J A. 2009. Characterization of the bovine pregnancy-associated glycoprotein gene family—analysis of gene sequences, regulatory regions within the promoter and expression of selected genes. BMC Genomics 10:185. doi:10.1186/1471-2164-10-185

Butler, J E 1980. Isolation and partial characterization of two bovine pregnancy-associated proteins. M.S. Thesis. University of Idaho.

Butler J E, Hamilton W C, Sasser R G, Ruder C A, Hass G M, Williams R J: Detection and partial characterization of two bovine pregnancy-specific proteins. Biol Reprod 26:925-933, 1982.

Camous S, Sharpigny G, Guillomot M, Martal J, Sasser R G: Purification of one bovine pregnancy-specific protein by high performance liquid chromatography (HPLC). Proc. Bard Workshop. Maternal Recognition of Pregnancy and Maintenance of the Corpus Luteum, Jerusalem, Abstract 2, 1988.

Eckblad, W P, Sasser, R G, Ruder C A, Panlasigui P., Kuczynski T. 1985: Localization of pregnancy-specific protein B (PSPB) in bovine placental cells using glucose oxidase-anti-glucose oxidase immunohistochemical stain. J. Anim. Sci. 61 (Suppl.): 149-150

Green J C, Okamura C S, Poock S E and Lucy M C. 2010. Measurement of interferon-tau (IFN-tau) stimulated gene expression inblood leukocytes for pregnancy diagnosis within 18-20 d after insemination in dairy cattle. Anim. Reprod. Sci., 121:24-33.

Hamilton, W C. 1979. Pregnancy-associated antigens of early pregnancy in cattle. M. S, Thesis. University of Idaho.

Hicks B A, Etter S J, Carnahan K G, Joyce M M, Assiri A A, Carling S J, Kodali K, Johnson G A, Hansen T R, Mirando M A, Woods G L, Vanderwall D K, and Ott T L. 2003. Expression of the uterine Mx protein in cyclic and pregnant cows, gilts, and mares. J. Anim. Sci. 81:1552-1561.

Howard, J M, Gabor G, Gray T., Passayant C, Ahmadzadeh A, Sasser N, Pals D, and Sasser S. 2007. BioPRYN a blood based pregnancy test for managing breeding and pregnancy in cattle. Proc. Western Section Amer. Soc. Anim. Sci 58:295-297.

Hughes A L, Green J A, Piontkivska H and Roberts R M. 2003. Aspartic Proteinase Phylogeny and the Origin of Pregnancy-Associated Glycoproteins. Molecular Biology and Evolution 20(11):1940-1945.

Humblot, P., Camous S, Martal J, Charlery J, Jeanguyot N, Thibier M and Sasser R G. 1988. Diagnosis of pregnancy by radioimmunoassy of a pregnancy-specific protein in plasma of dairy cows. Thereiogenology 30:257-268.

Ivani, K A. 1984. Diagnosis of pregnancy by radioimmunoassay of a pregnancy-specific protein in serum of cows. M.S. Thesis. University of Idaho.

King, Cathy. 1996. Presence of pregnancy-specific protein B in milk of postpartum cows. MS Thesis. University of Idaho.

Lynch R A, Alexander B M, Sasser R G. 1992. The cloning and expression of the pregnancy-specific protein B (bPSPB) gene. Biol Reprod 46(Suppl. 1):72.

Noyes, J. H., Sasser R G, Johnson B K, Bryant L D, and Alexander B. 1997. Accuracy of pregnancy detection by serum protein (PSPB) in elk. Wildlife Society Bulletin 25:695-698.

Sasser R G, Crock J., Ruder-Montgomery C A. 1989 Characteristics of pregnancy-specific protein B in Cattle. J Reprod Fertil 37:109-113 (Suppl.).

Sasser R G, Ruder C A. 1987. Detection of early pregnancy in domestic ruminants. J Reprod Fertil 34:261-271.

Sasser R G, Ruder C A, Ivani K A, Butler J E, Hamilton W C. 1986. Detection of pregnancy by radioimmunoassay of a novel pregnancy-specific protein in serum of cows and a profile of serum concentrations during gestation. Biol Reprod 35:936-942.

Sasser R G, Hamilton W C. U.S. Pat. No. 4,554,256. Novel antigen associated with early detection of mammalian pregnancy. Nov. 19, 1985.

Sasser R G, Hamilton W C. U.S. Pat. No. 4,705,748. Antigen associated with early detection of mammalian pregnancy. A continuation of U.S. Pat. No. 4,554,256, Nov. 10, 1987.

Semambo, D K N, Eckersall P D, Sasser R G and Ayliffe T R. 1992. Pregnancy-specific protein B and progesterone in monitoring viability of the embryo in early pregnancy in the cow after experimental infection with *Actinomyces pyogenes*. Theriogenology 37:741-748.

Stabenfeldt G H, Daels P F, Munro C J, Kindahl H, Hughes J P, Lasley B. 1991. An oestrogen conjugate enzyme immunoassay for monitoring pregnancy in the mare: limitations of the assay between days 40 and 70 of gestation. J. Reprod. Fertil. 44:37-44.

Szafranska B., Panasiewicz G, and Majewska M. 2006. Biodiversity of multiple Pregnancy-Associated Glycoprotein (PAG) family: gene cloning and chorionic protein purification in domestic and wild eutherians (Placentalia)—a review. Reprod. Nutr. Dev. 481-502.

Willard J M, White D R, Wesson C A R, Stellflug J and Sasser R G. 1995. Detection of fetal twins in sheep using a radioimmunoassay for pregnancy-specific protein. Journal of Animal Science 73 960-966.

Xie S, Low B G, Nagel R J, Kramer K K, Anthony R V, Zoli A P, Beckers J-F, Roberts R M: Identification of the major pregnancy-specific antigens of cattle and sheep as inactive members of the aspartic proteinase family. Proc Natl Acad Sci USA 88:10247-10251, 1991.

Zoli A P, Beckers J-F, Souters-Ballman P, Closset J, Falmagne P, Ectors F: Purification and characterization of a bovine pregnancy-associated glycoprotein. Biol Reprod 45: 1-10, 1991.

U.S. Pat. Nos. 4,554,256; 4,668,621; 4,705,748; 5,559,097; 6,869,770; 7,393,696; and 7,575,861.

U.S. Patent Application Numbers 2005/0100975; 2006/0199235; 2007/0166773; 2007/0184558 and 2008/0026384.

Although the present disclosure has been provided with reference to the foregoing operational principles and embodiments, it will be apparent to those skilled in the art that various changes in form and detail may be made without departing from the spirit and scope of the disclosure. The present disclosure is intended to embrace all such alternatives, modifications, and variances. Where the disclosure recites "a," "a first," or "another" element, or the equivalent thereof, it should be interpreted to include one or more such elements, neither requiring nor excluding two or more such elements. Furthermore, any aspect shown or described with reference to a particular embodiment should be interpreted to be compatible with any other embodiment, alternative, modification, or variance.

We claim:

1. A method of determining whether a non-human animal is pregnant comprising:
   providing a test kit including at least three test surfaces, each surface being coated with a first biomolecular recognition element specific to a marker of pregnancy, a first reagent solution including a second biomolecular recognition element specific to the marker, a first standard corresponding to a first amount of the marker, and a second standard corresponding to a second amount of the marker that is lower than the first amount,
   obtaining a first sample from the animal after insemination of the animal,
   introducing equal aliquots of the first reagent solution to each of the three surfaces,
   introducing the first standard to a first one of the surfaces,
   introducing the second standard to a second one of the surfaces,
   introducing the sample to a third one of the surfaces,
   allowing the standards and sample to react with the first biomolecular recognition element to bind any of the marker present to the three surfaces, and the second biomolecular recognition element to react with the marker bound to each of the three surfaces, under a substantially constant temperature for a specified time period,
   removing unbound materials, including unbound marker, unbound standards, unbound sample, and unbound first reagent solution, from the three test surfaces,
   introducing to the three surfaces a visual indicator to undergo a visually detectable change, the magnitude of which is related to the amount of the second biomolecular recognition element bound to each surface,
   comparing under a substantially constant temperature after a specified time period the visual indicator present in the third one of the surfaces with the visual indicators present in the first and second surfaces,
   comparing a magnitude of the visual indictor from the first sample on the third surface to respective magnitudes from the first standard on the first surface and the second standard on the second surface without using a spectrophotometer,
   determining that the animal is pregnant as indicated by the magnitude of the visual indicator of the third surface being greater than that of the first surface,
   determining that the animal is not pregnant as indicated by the magnitude of the visual indicator of the third surface being lower than that of the second surface,
   determining that a retest of the animal for pregnancy is required as indicated by the magnitude of the visual indicator of the third surface being between the magnitudes of the visual indicators of the first and second surfaces, and
   retesting a second sample retrieved at a time after the first sample was retrieved based on the determination that the animal requires retesting to determine pregnancy.

2. The method of claim 1, wherein the first and second biomolecular recognition elements are detection antibodies that are monoclonal or polyclonal.

3. The method of claim 1, wherein the sample and the standards are permitted to bind to the first biomolecular recognition elements on each surface before introducing the first reagent solution to each surface.

4. The method of claim 1, wherein the first reagent solution is introduced to each surface before introducing the sample and the standards to each surface.

5. The method of claim 1, wherein the second biomolecular recognition element is a detection antibody conjugated with the visual indicator.

6. The method of claim 5, wherein the visual indicator is fluoroscein.

7. The method of claim 1, wherein the second biomolecular recognition element is a detection antibody conjugated with an enzyme.

8. The method of claim 7, further comprising introducing to each test surface equal amounts of a second reagent solution with the visual indicator that is capable of reacting with the enzyme, and
   allowing the visual indicator to react, under a substantially constant temperature for a specified time period, with the enzyme bound to the three surfaces to generate the visually detectable change.

9. The method of claim 7, wherein the enzyme is horseradish peroxidase and the visual indicator is 3,3',5,5'-tetramethylbenzidine (TMB).

10. The method of claim 1, wherein the second biomolecular recognition element is a detection antibody conjugated with a hapten.

11. The method of claim 10, further comprising:
    introducing equal amounts of a second reagent solution including an enzyme capable of binding to the hapten,
    allowing the enzyme to react with the hapten-conjugated second detection antibody bound to the three surfaces under a substantially constant temperature for a specified time period,
    removing unbound enzyme and unbound second reagent solution from the three test surfaces,
    introducing to each of the three test surfaces equal amounts of a third reagent solution with the visual indicator that is capable of binding to the enzyme, and
    allowing the visual indicator to react, under a substantially constant temperature for a specified time period, with the enzyme bound to the surfaces of the three surfaces to generate the visually detectable change.

12. The method of claim 11, wherein the hapten is biotin, the enzyme is horseradish peroxidase conjugated with strepavidin, and the visual indicator is 3,3',5,5'-tetramethylbenzidine (TMB).

13. The method of claim 10, further comprising:
introducing to each of the three test surfaces equal amounts of a second reagent solution including the visual indicator that is capable of binding with the hapten-conjugated second detection antibody, and
allowing the visual indicator to react with the hapten bound to the three surfaces under a substantially constant temperature for a specified time period to generate the visually detectable change.

14. The method of claim 13, wherein the visual indicator is fluroscein.

15. The method of claim 1, wherein each test surface is sealed with a preserving agent derived from a blocking solution that includes a buffering agent, a non-reducing sugar, and a blocking agent, further wherein the preserving agent allows for storage of the sealed, coated test surfaces at room temperature for about 14 weeks while retaining substantially the same signal as that of an unsealed, coated test surface after about one day.

16. The method of claim 15, wherein the buffering agent includes $NaH_2PO4$, $Na_2HPO4$, and NaCl, the non-reducing sugar is sucrose, and the blocking agent is bovine serum albumin.

17. The method of claim 1, wherein the marker is pregnancy-specific protein B (PSPB), the animal is a ruminant, and the second sample is retrieved from the ruminant about 3 days to about 7 days after the first sample was retrieved from the ruminant.

18. The method of claim 1, wherein the marker is a protein, a carbohydrate or a lipid.

19. A method of determining whether a non-human animal is pregnant comprising:
providing a test kit including at least three test surfaces, each surface being coated with a first biomolecular recognition element specific to a marker of pregnancy, a first reagent solution including a second biomolecular recognition element specific to the marker, a first standard corresponding to a first amount of the marker, and a second standard corresponding to a second amount of the marker that is lower than the first amount,
obtaining a first sample from the animal after insemination of the animal,
introducing equal aliquots of the first reagent solution to each of the three surfaces,
introducing the first standard to a first one of the surfaces,
introducing the second standard to a second one of the surfaces,
introducing the sample to a third one of the surfaces,
allowing the standards and sample to react with the first biomolecular recognition element to bind any of the marker present to the three surfaces, and the second biomolecular recognition element to react with the marker bound to each of the three surfaces, under a substantially constant temperature for a specified time period,
removing unbound materials, including unbound marker, unbound standards, unbound sample, and unbound first reagent solution, from the three test surfaces,
introducing to the three surfaces a visual indicator to undergo a visually detectable change, the magnitude of which is related to the amount of the second biomolecular recognition element bound to each surface,
visually comparing with the naked eye, without the aid of an instrument, under a substantially constant temperature, and after a specified time period, a color intensity of the visual indicator present in the third one of the surfaces with respective color intensities of the visual indicators present in the first and second surfaces,
determining, based on the visually comparing step, whether a magnitude of the color intensity of the third surface is greater than that of the first surface, is equal to or greater than that of the first surface and equal to or less than that of the second surface, or is less than that of the second surface,
concluding that the animal is pregnant when the magnitude of the color intensity of the visual indicator of the third surface is greater than that of the first surface,
concluding that the animal is not pregnant when the magnitude of the color intensity of the visual indicator of the third surface is lower than that of the second surface, and
concluding that retesting is required of a second sample from the animal, retrieved at a time after the first sample was retrieved, if the magnitude of the color intensity of the visual indicator of the third surface is between the magnitudes of the visual indicators of the first and second surfaces, and
retesting the second sample to visually determine with the naked eye, without the aid of an instrument, whether the second sample indicates that the cow is pregnant, not pregnant, or another retest is required, wherein the second sample is retrieved from the animal between 24 hours and 7 days after the first sample was retrieved from the animal.

20. The method of claim 19, further comprising introducing the first reagent solution to each surface before introducing the sample and the standards to each surface.

21. The method of claim 19, wherein the second biomolecular recognition element is a detection antibody conjugated with an enzyme.

22. The method of claim 19, wherein the marker is pregnancy-specific protein B (PSPB), the animal is a ruminant, and the second sample is retrieved from the ruminant about 3 days to about 7 days after the first sample was retrieved from the ruminant.

23. The method of claim 19, further comprising using an enhancer to increase the intensity of the color magnitudes to give an increase in the spread or dynamic range between the first and second standards to create better color magnitude separation between the first and second standards, thereby enabling an easier visual comparison of the magnitudes of color intensities of the respective visual indicators of the first, second and third test surfaces.

24. The method of claim 1, further comprising visually comparing the magnitudes of color intensities of the respective visual indicators of the first, second and third test surfaces without using optical density readings to determine the magnitudes of color intensities of the respective visual indicators of the first, second and third test surfaces.

25. The method of claim 1, further comprising visually comparing the magnitudes of color intensities of the respective visual indicators of the first, second and third test surfaces with one of an unaided naked eye without an instrument, and a handheld reader.

26. The method of claim 25, further comprising using an enhancer to increase the intensity of the color magnitudes to give an increase in the spread or dynamic range between the first and second standards to create better color magnitude separation between the first and second standards, thereby enabling an easier visual comparison of the magnitudes of color intensities of the respective visual indicators of the first, second and third test surfaces.

27. The method of claim 21, further comprising providing the enzyme as horseradish peroxidase conjugated with strepavidin as an enhancer.

28. The method of claim 1, further comprising validating proper calibration of the first and second standards by visually comparing to ensure that the first standard has a higher magnitude of color intensity than the second standard.

29. The method of claim 1, further comprising validating proper calibration of the first and second standards by visually comparing the magnitude of intensities of the first and second standards to a color card that includes indications of proper-calibrated color intensity of the first and second standards.

* * * * *